United States Patent [19]

Zipperer et al.

[11] Patent Number: 5,175,167

[45] Date of Patent: Dec. 29, 1992

[54] HETARYLALKENES, THEIR PREPARATION AND INTERMEDIATES FOR THEIR PREPARATION AND THEIR USE

[75] Inventors: Bernhard Zipperer, Dirmstein; Manfred Lauer, Ludwigshafen; Norbert Goetz, Worms; Thomas Zierke, Boehl-Iggelheim; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 652,634

[22] Filed: Feb. 8, 1991

[30] Foreign Application Priority Data

Feb. 9, 1990 [DE] Fed. Rep. of Germany ....... 4003919

[51] Int. Cl.⁵ ................... A01N 43/40; C07D 213/26; C07D 213/30; C07D 213/32
[52] U.S. Cl. .................................. 514/277; 514/247; 514/252; 514/255; 514/256; 514/357; 514/358; 514/332; 514/336; 544/224; 544/238; 544/242; 544/295; 544/333; 544/296; 544/335; 544/336; 544/405; 546/266; 546/267; 546/283; 546/284; 546/329; 546/330; 546/334; 546/339; 546/340; 546/344; 546/346
[58] Field of Search ............... 546/255, 262, 266, 267, 546/283, 284, 330, 339, 340, 344, 345, 346, 329, 334; 544/333, 405; 514/277, 332, 336, 252, 256, 357, 358

[56] References Cited

U.S. PATENT DOCUMENTS

| | | | |
|---|---|---|---|
| 4,512,995 | 4/1985 | Rose | 546/344 |
| 4,600,712 | 7/1986 | Haken et al. | 514/188 |
| 5,036,074 | 7/1991 | Isenring et al. | 546/346 |

FOREIGN PATENT DOCUMENTS

| | | | |
|---|---|---|---|
| 0214566 | 3/1987 | European Pat. Off. | |
| 298380 | 1/1989 | European Pat. Off. | 546/340 |
| 409077 | 1/1991 | European Pat. Off. | |

OTHER PUBLICATIONS

NASU et al., Chemical Abstracts, vol. 108, No. 112429 (1988) (Abstract for JP 86/12628 Jan. 23, 1986).
Woltersdorf et al., J. Med. Chem. 20 p. 1400 (1977).

Primary Examiner—Mukund J. Shah
Assistant Examiner—E. Bernhardt
Attorney, Agent, or Firm—Oblon, Spivak, McClelland, Maier & Neustadt

[57] ABSTRACT

Hetarylalkenes of the general formula I $$Ar-CH=\underset{A}{\underset{|}{C}}-Z-B \qquad I$$

where
Ar is hetaryl,
A is $C_1$–$C_6$-alkyl, $C_2$–$C_6$-alkenyl, $C_3$–$C_8$-cycloalkyl, $C_3$–$C_8$-cycloalkyl-$C_1$–$C_3$-alkyl or unsubstituted or monosubstituted, disubstituted or trisubstituted aryl or aralkyl, $$-\underset{}{\overset{O}{\underset{\|}{C}}}-,\ -\underset{}{\overset{OR}{\underset{|}{C}H}}-,\ -\underset{}{\overset{SR^1}{\underset{|}{C}H}}-,\ -\underset{}{\overset{Hal}{\underset{|}{C}H}}-\ \text{or}\ -\underset{}{\overset{CN}{\underset{|}{C}H}}-$$

Z is
where
R is hydrogen, $C_2$–$C_4$-acyl, unsubstituted or substituted benzoyl, $C_1$–$C_4$-alkylsulfonyl, unsubstituted or $C_1$–$C_4$-alkyl-substituted phenylsulfonyl or a radical $R^1$,
$R^1$ is $C_1$–$C_4$-alkyl or unsubstituted or substituted phenyl or benzyl
and Hal is fluorine, chlorine, bromine or iodine,
and B is unsubstituted or substituted mononuclear or dinuclear aryl, aralkyl or hetaryl,
and their N-oxides and addition salts, the preparation of these substances, intermediates for this purpose and the preparation thereof, fungicides containing hetarylalkenes and a corresponding method for controlling harmful fungi.

4 Claims, No Drawings

HETARYLALKENES, THEIR PREPARATION AND INTERMEDIATES FOR THEIR PREPARATION AND THEIR USE

The present invention relates to novel hetarylalkenes of the general formula I

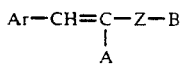

where

Ar is 3-pyridyl, 3-pyridazinyl, 5-pyrimidinyl or 2-pyrazinyl;

A is $C_1$-$C_6$-alkyl, $C_2$-$C_6$-alkenyl, $C_3$-$C_8$-cycloalkyl, $CC_3$-$C_8$-cycloalkyl-$C_1$-$C_3$-alkyl, mononuclear, dinuclear or trinuclear aryl or aralkyl, where aryl in each case may be monosubstituted, disubstituted or trisubstituted by $C_1$-$C_4$-alkyl, $C_1$-$C_4$-alkoxy, $C_1$-$C_4$-mono-, di- or trihaloalkyl, $C_1$-$C_4$-haloalkoxy, phenyl or halogen;

Z is

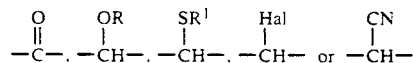

where

R is hydrogen, $C_1$-$C_4$-alkyl, $C_2$-$C_4$-acyl, phenyl, benzyl or benzoyl, in which each of the phenyl rings may be monosubstituted, disubstituted or trisubstituted by $C_1$-$C_4$alkyl, $C_1$-$C_4$-alkoxy, $C_1$-$C_4$-haloalkyl, $C_1$-$C_4$-haloalkoxy, halogen, cyano or nitro, or is $C_1$-$C_4$-alkylsulfonyl or unsubstituted or $C_1$-$C_4$-alkyl-substituted phenylsulfonyl, R is $C_1$-$C_4$-alkyl, phenyl or benzyl, where each of the phenyl rings may be monosubstituted, disubstituted or trisubstituted by $C_1$-$C_4$-alkyl, $C_1$-$C_4$-alkoxy, $C_1$-$C_4$-haloalkyl, $C_1$-$C_4$-haloalkoxy, halogen, cyano or nitro, and Hal is fluorine, chlorine, bromine or iodine; and B is mononuclear or dinuclear aryl, aralkyl or hetaryl, and, if Z is >CO, hetaryl has no $sp^3$-hybridized nitrogen atom directly adjacent to Z, and in which each of the aromatic rings may be monosubstituted, disubstituted or trisubstituted by $C_1$-$C_4$-alkyl, $C_1$-$C_4$-alkoxy, $C_1$-$C_4$-haloalkyl, $C_2$-$C_4$-haloalkoxy, phenyl, halophenyl or halogen, and their N-oxides and addition salts with inorganic mineral acids, carboxylic acids or mononuclear arylsulfonic acids.

The present invention furthermore relates to processes for the preparation of these compounds and also to intermediates, processes for the preparation of intermediates, the fungicides containing hetarylalkenes I and a method for controlling harmful fungi with the aid of the hetarylalkenes I or these fungicides.

Fungicidal hetarylalkenes, for example

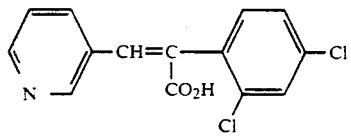

are disclosed in EP-A2-104 690. However, the fungicidal action of most of these compounds is unsatisfactory.

It is an object of the present invention to provide particularly active fungicidal compounds.

We have found that this object is achieved by the hetarylalkenes I defined at the outset.

With regard to the intended use of the hetarylalkenes as fungicides, preferred substituents are the following radicals:

Ar is 3-pyridyl, 5-pyrimidinyl, 3-pyridazinyl or 2-pyrazinyl,

A is methyl, ethyl, n-propyl, isopropyl, n-butyl, isobutyl, tert-butyl, n-pentyl, isopentyl, neopentyl, n-hexyl, neohexyl, cyclopropyl, cyclopentyl, cyclohexyl, cycloheptyl, cyclooctyl, cyclopropylmethyl, cyclopentylmethyl, cyclohexylmethyl, 2-cyclohexylethyl, 3-cyclohexylpropyl, phenyl, mono-, di- or trimethylphenyl, tert-butylphenyl, mono-, di- or trimethoxyphenyl, n-butoxyphenyl, tert-butoxyphenyl, trifluoromethylphenyl, difluoromethoxyphenyl, trifluoromethoxyphenyl, tetrafluoroethoxyphenyl, biphenyl, mono-, di- or trifluorophenyl, mono-, di- or trichlorophenyl, chlorofluorophenyl, benzyl, mono-, di- or trimethylbenzyl, mono-, di- or trichlorobenzyl, fluorobenzyl, 2-phenylethyl, mono-, di- or trimethylphenylethyl, mono-, di- or trichlorophenylethyl, fluorophenylethyl or 3-phenylpropyl, B is phenyl, mono-, di or trimethylphenyl, ethylphenyl, isopropylphenyl, tert-butylphenyl, naphthyl, mono-, di- or trimethoxyphenyl, n-butoxyphenyl, tert-butoxyphenyl, trifluoromethylphenyl, difluoromethoxyphenyl, trifluoromethoxyphenyl, tetrafluoroethoxyphenyl, biphenyl, chlorobiphenyl, mono-, di- or trichlorophenyl, mono-, di- or trifluorophenyl, chlorofluorophenyl, bromophenyl, benzyl, mono-, di- or trimethylbenzyl, fluorobenzyl, mono-, di- or trichlorobenzyl, chlorofluorobenzyl, pyridyl, chloropyridyl, methylpyridyl, pyrimidinyl, pyrazinyl, thienyl or furyl Z is

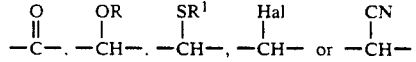

where R is preferably hydrogen, methyl, ethyl, n-propyl, isopropyl, n-butyl, tert-butyl, acetyl, propionyl, butyryl, phenyl, mono-, di- or trimethylphenyl, tert-butylphenyl, mono-, di- or trimethoxyphenyl, trifluoromethylphenyl, fluorophenyl, mono-, or dichlorophenyl, bromophenyl, cyanophenyl, mono- or dinitrophenyl, benzyl, methylbenzyl, methoxybenzyl, trifluoromethylbenzyl, fluorobenzyl, mono- or dichlorobenzyl, bromobenzyl, cyanobenzyl, mono- or dinitrobenzyl, benzoyl, methylbenzoyl, fluorobenzoyl, mono-, di- or trichlorobenzoyl, bromobenzoyl, cyanobenzoyl or mono- or dinitrobenzoyl, $R^1$ is preferably methyl, ethyl, n-propyl, isopropyl, n-butyl, tert-butyl, phenyl, mono-, di- or trimethylphenyl, tert-butylphenyl, mono-, di- or trimethoxyphenyl, trifluoromethylphenyl, fluorophenyl, mono- or dichlorophenyl, bromophenyl, cyanophenyl, mono- or dinitrophenyl, benzyl, methylbenzyl, methoxybenzyl, trifluoromethylbenzyl, fluorobenzyl, mono- or dichlorobenzyl, bromobenzyl, cyanobenzyl or mono- or dinitrobenzyl and Hal is, in particular, fluorine, chlorine or bromine.

Particularly preferred compounds are those in which A is ethyl, n-propyl, n-butyl, tert-butyl, n-pentyl, neopentyl, n-hexyl, phenyl or 4-fluorophenyl, B is phenyl, 2-chlorophenyl, 4-chlorophenyl, 2,4-dichlorophenyl, 4-fluorophenyl, 2-methylphenyl, 4-methylphenyl, 2,4-dimethylphenyl, 2,6-dimethylphenyl, 2,4,6-trimethylphenyl, 4-biphenyl or 3-pyridyl; and Ar is 3-pyridyl. Compounds which are particularly suitable as fungicides are E-1-(2,4-dichlorophenyl)-2-(3-pyridylmethylidene)-4,4-dimethylpentan-1-ol, E-1-(2,4-dimethylphenyl)-2-(3-pyridylmethylidene)-hexan-1-ol, E-1-(2,4-dichlorophenyl)-2-(3-pyridylmethylidene)-3,3-dimethylbutan-1-ol, E-1-(2,4-dichlorophenyl)-2-(3-pyridylmethylidene)-hexan-1-ol and E-1-(2,4-dichlorophenyl)-2-(3-pyridylmethylidene)-octan-1-ol.

The hetarylalkenes I contain an asymmetrically substituted C=C double bond. They can therefore occur as E/Z isomer mixtures or in the form of the pure isomers. The pure isomers can be obtained from the isomer mixtures by known separation methods, such as fractional crystallization or chromatography. The present invention relates both to the individual isomeric compounds and to mixtures thereof.

The hetarylalkenols Ia are obtained, for example, by reacting a hetarylalkenal II with an organolithium compound Li-B or with a Grignard reagent B-MgHal, where Hal is chlorine, bromine or iodine, in a conventional manner. The reaction is carried out in an inert solvent, preferably an ether, such as diethyl ether, tetrahydrofuran or methyl tert-butyl ether or in a mixture of these ethers. It is advisable initially to take the organometallic compound and to meter in the hetarylalkenal II in the liquid phase at from −70° to 50°C. In the case of the organolithium compounds, the reaction is advantageously carried out at from −70° to 0° C., preferably from −70° to −30°C. The temperatures in the reactions with the Grignard reagents are generally chosen at from 0° to 50° C., in particular from 20° to 50°C. The stated starting materials are advantageously used in a molar ratio of from 0.5:1 to 2:1.

The hetarylalkenals II, in which A is methyl or unsubstituted or substituted phenyl, are disclosed in J. Org. Chem. 43 (1978), 3396 and EP-A2-298 380. The novel hetarylalkenals II in which Ar is 3-pyridazinyl, 5-pyrimidinyl or 2-pyrazinyl, preferably 3-pyridyl, and D is $C_2$-$C_6$-alkyl, preferably ethyl, n-propyl, isopropyl, n-butyl or tert-butyl, $C_3$-$C_8$-cycloalkyl, in particular cyclopropyl, cyclopentyl or cyclohexyl, $C_3$-$C_8$-cycloalkyl-$C_1$-$C_3$-alkyl, especially cyclopropylmethyl, cyclopentylmethyl, cyclohexylmethyl, 2-cyclohexylethyl or 3-cyclohexylpropyl, or mononuclear or dinuclear aryl-$C_1$-$C_3$-alkyl, preferably benzyl, chlorobenzyl, fluorobenzyl, 2-phenylethyl, chlorophenylethyl, fluorophenylethyl or 3-phenylpropyl, can be prepared similarly to the process disclosed in EP-A2-298 380, by aldol condensation of D-CH$_2$CHO with ArCHO (cf. also Houben-Weyl, Methoden der organischen Chemie, Vol. III/1, page 76 et seq.).

The starting materials of the type D-CH$_2$CHO are readily obtainable where D is alkyl and can be prepared by known methods (cf. Houben-Weyl, Volume 7/1, pages 55 et seq., 76 et seq., 159 et seq.) in the case of the other radicals.

3-Formylpyridine is generally known and readily obtainable. The syntheses of the other aldehydes of the type Ar—CHO are described in, for example, the standard work The Chemistry of Heterocyclic Compounds (A. Weissberger and E. C. Taylor) (3-formylpyridazine: The Pyridazines, R. N. Castle, Editor, page 365, John Wiley & Sons, New York, 1973; 2-formylpyrazine: The Pyrazines, G. B. Barlin, Editor, page 294 et seq., John Wiley & Sons, New York, 1982; 5-formylpyrimidine: The Pyrimidines, Suppl. I, D. J. Brown, page 127, John Wiley & Sons, New York, 1970).

The organometallic compounds Li-B and HalMgB can be prepared by known processes, as described in Houben-Weyl, Methoden der organischen Chemie, Vol. XIII/1, page 87 et seq. and ibid. XIII/2a, page 54 et seq., from B-Hal and Li or Mg.

In a second method for the preparation of the hetarylalkenols Ia, a hetarylaldehyde ArCHO is reacted with a ketone of the type

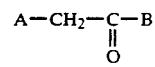

to give the hetarylalkenone Ib. The hetarylalkenone Ib can then be reduced to the hetarylalkenol Ia by conventional methods. Ar, A and B have the meanings stated in claim 1.

The aldol condensation of the hetarylaldehyde ArCHO with the ketone

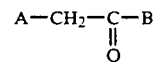

is carried out in the presence of a basic or acidic catalyst (cf. Houben-Weyl, Methoden der organischen Chemie, Vol. VII/1, page 76 et seq.). Examples of suitable basic catalysts are alkali metal or alkaline earth metal hydroxides, such as sodium, potassium, calcium or barium hydroxide, alkali metal alcoholates, such as sodium or potassium methylate, ethylate, propylate or butylate, and amines, such as diethylamine, triisopropylamine, dicyclohexylamine, pyrrolidine or piperidine. Examples of suitable acidic catalysts are weak acids, such as acetic acid, oxalic acid, boric acid and sulfonic acids, such as methanesulfonic acid, benzenesulfonic acid and p-toluenesulfonic acid, and salts of weak acids with amines, such as piperidine acetate, pyrrolidine acetate, ethylenediamine tetraacetate, pyridine methanesulfonate or pyridine p-toluenesulfonate.

Examples of suitable solvents are alcohols, such as methanol, ethanol, propanol, isopropanol, butanol or tert-butanol, ethers, such as diethyl ether, methyl tert-butyl ether, tetrahydrofuran or dioxane, or hydrocarbons, such as cyclohexane, benzene, toluene or xylene.

The reaction is carried out as a rule at from 0 to 60°C.

The molar ratio of the starting materials is from 0.5:1 to 5:1 (ArCHO/ketone) and the molar ratio of ArCHO to the catalyst is from 1:1 to 100:1.

The starting compounds of the type

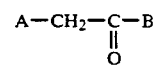

can be prepared, for example, in a known manner from carbonyl chlorides and aromatics by Friedel-Crafts acylation (cf. Houben-Weyl, Volume 7/2a, page 15 et seq.).

The hetarylalkenones Ib can be reduced by conventional methods to the hetarylalkenols Ia already described (cf. Houben-Weyl, Methoden der organischen Chemie, Vol. IV, 1d, page 297 et seq.). Examples of suitable reducing agents are complex hydrides, such as lithium aluminum hydride, lithium trimethoxyaluminum hydride, sodium borohydride or sodium cyanoborohydride, and aluminum alcoholates, such as aluminum isopropylate or aluminum cyclohexylate (cf. M. Hudlicky, Reductions in Organic Chemistry, page 119 et seq., Ellis Horward Series, Chichester, 1984). The solvents used for the reductions are, for example, ethers, such as diethyl ether, tetrahydrofuran, dimethoxyethane or dioxane, or alcohols, such as methanol, ethanol, n-propanol, iso-propanol or cyclohexanol, depending on the reducing agent.

In the reduction with complex hydrides, it is advisable to carry out the reaction at from −30° to 20° C., whereas higher temperatures, in particular the boiling point of the free alcohol from which the aluminum alcoholate is derived, are advantageous when aluminum alcoholates are used.

Sodium borohydride or sodium cyanoborohydride in methanol or ethanol is preferably used. The ratio of the number of equivalents of hetarylalkenone Ib to reducing agent is, as a rule, from 1:1 to 1:2.

The novel hetarylalkenols Ia can be esterified or etherified to the hetarylalkene esters or ethers Ic. For this purpose, the hetarylalkenols Ia are reacted with alkylating or acylating agents R-X in a conventional manner (cf. Houben-Weyl, Volume 6/1b, pages 800 et seq., 823 et seq.). Here, R is $C_1-C_4$-alkyl, in particular methyl, ethyl, isopropyl or tert-butyl, $C_2-C_4$-acyl, preferably acetyl or propionyl, benzyl or benzoyl, where the phenyl radicals may be monosubstituted, disubstituted or trisubstituted by $C_1-C_4$-alkyl, such as methyl, ethyl, propyl or butyl, $C_1-C_4$-alkoxy, such as methoxy, ethoxy or propoxy, $C_1-C_4$-haloalkyl, especially trifluoromethyl, $C_1-C_4$-haloalkoxy, such as tetrafluoroethoxy, halogen, such as fluorine, chlorine or bromine, cyano or nitro, or is $C_1-C_4$-alkylsulfonyl, in particular methanesulfonyl or unsubstituted or $C_1-C_4$-alkyl-substituted phenylsulfonyl, and X is, for example, chlorine, bromine, iodine, acetyl or, if R itself is not a sulfo group, methanesulfonyl, benzenesulfonyl or p-toluenesulfonyl.

The reaction is carried out as a rule at from 0° to 100°C.

The type of solvent depends on the type of radical R. If R is alkyl or benzyl, preferably used solvents are ethers, such as diethyl ether, tetrahydrofuran, dioxane or dimethoxyethane, or amides, such as N,N-dimethylformamide, N-methylpyrrolidone, N,N-dimethylethyleneurea, N,N-dimethylpropyleneurea. An addition of an equimolar amount of a base, in particular sodium hydride, is also advisable.

If R is acyl, benzoyl or a sulfonyl halide, preferably used diluents are halogenated or halogen-free hydrocarbons, such as dichloromethane or trichloromethane, toluene or xylene, or an excess of a base which acts as a catalyst, preferably tertiary amines, such as triethylamine, tripropylamine or pyridine.

Hetarylalkene esters Ic in which R is sulfo can be converted into hetarylalkenes of the general formula Id by conventional methods (cf. Houben-Weyl, Vol. 9, page 343 et seq.) by reaction with halides, cyanides, hydrogen sulfides, alcohols or thiols.

Preferably used halides, cyanides or hydrogen sulfides are alkali metal, alkaline earth metal, ammonium or tetraalkylammonium salts. Examples are lithium cyanide, sodium cyanide, potassium cyanide, tetramethylammonium cyanide, tetrabutylammonium cyanide, tetrabutylammonium fluoride, tetrabutylammonium chloride, tetrabutylammonium bromide, tetrabutylammonium iodide, lithium fluoride, lithium chloride, lithium bromide, lithium iodide, sodium fluoride, sodium chloride, sodium bromide, sodium iodide, potassium fluoride, potassium chloride, potassium bromide, potassium iodide, sodium hydrogen sulfide and potassium hydrogen sulfide.

Particularly preferred alcohols are phenols which may be monosubstituted, disubstituted or trisubstituted, inparticular phenol, mono-, di- or trimethylphenol, tert-butylphenol, mono-, di- or trimethoxyphenol, trifluoromethylphenol, fluorophenol, chlorophenol or bromophenol.

Particularly suitable thiols are $C_1-C_4$-alkanethiols, such as methane-, ethane-, n-propane-, isopropane-, n-butane-, isobutane-, sec-butane- or tertbutanethiol, and unsubstituted or monosubstituted, disubstituted or trisubstituted thiophenols or thiobenzyl alcohols, such as thiophenol, mono-, di- or trimethylthiophenol, tert-butylthiophenol, mono-, di- or trimethoxythiophenol, fluoro- or chlorothiophenol, thiobenzyl alcohol, mono-, di- or trimethylthiobenzyl alcohol, tert-butylthiobenzyl alcohol, mono-, di- or trimethoxythiobenzyl alcohol, fluoro- or chlorothiobenzyl alcohol or cyano- or nitrothiobenzyl alcohol.

Polar, inert solvents, such as ethers, especially tetrahydrofuran or dioxane, ketones, in particular acetone, methyl ethyl ketone or methyl isobutyl ketone, nitriles, preferably acetonitrile or propionitrile, amides, for example N,N-dimethylformamide, N-methylpyrrolidone, N,N-dimethylethyleneurea or N,N-dimethylpropyleneurea, sulfoxides, in particular dimethyl sulfoxide, sulfones, e.g. sulfolane, alcohols, preferably methanol, ethanol, n-propanol, isopropanol, n-butanol or tert-butanol, or mixtures of these substances are suitable for the reaction. In the reaction of the hetarylalkene esters Ic with phenols or thiols, auxiliary bases are used, especially alkali metal and alkaline earth metal hydroxides, such as sodium hydroxide or potassium hydroxide, alkali metal and alkaline earth metal carbonates, such as sodium carbonate, potassium carbonate or calcium carbonate, alkali metal and alkaline earth metal alcoholates, such as sodium methylate, sodium ethylate, sodium propylate, sodium isopropylate, potassium isopropylate or potassium tert-butylate, and tertiary amines, such as triethylamine, tripropylamine or pyridine.

The reaction is carried out as a rule at from 20° to 100°C.

The oxidation of the hetarylalkenes I to the corresponding N-oxides is carried out by conventional methods. Examples of suitable oxidizing agents are per acids or per acids produced in situ from hydrogen peroxide and carboxylic anhydrides, or hydrogen peroxide or organic derivatives of hydrogen peroxide (cf. for example R. A. Abramovitch and E. M. Smith in Chemistry of Heterocyclic Compounds, Volume 14, Suppl. 2, page 1 et seq., John Wiley, New York, 1974; A. R. Katritzky and J. M. Lagouski, The Chemistry of Heterocyclic N-oxides, page 21 et seq., Academic Press, New York, 1971).

The preparation of the acid addition salts of the hetarylalkenes I is likewise carried out by conventional methods.

An overview of the stated preparation processes for the hetarylalkenes I is shown in the scheme below:

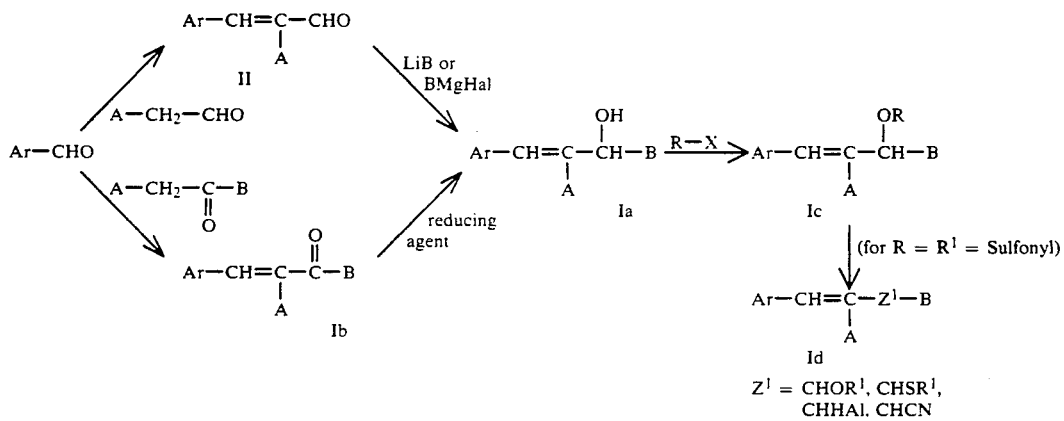

Scheme: Overview of the preparation processes for the hetarylalkenes I $Z^1$ = CHOR$^1$, CHSR$^1$, CHHAl, CHCN The Examples which follow illustrate the preparation of the novel compounds.

1. Preparation of E-1-(4-fluorophenyl)-2-(3-pyridylmethylidene)-1-hexanol via E-2-(3-pyridylmethylidene)-hexanal 6.0 g (0.15 mol) of sodium hydroxide were added to a solution of 160.5 g (1.5 mol) of pyridine-3-carbaldehyde in 750 ml of methanol. Thereafter, 150.0 g (1.5 mol) of hexanal were added dropwise in the course of 3 hours at room temperature. Stirring was carried out for 1 hour, the pH was brought to 6 with acetic acid and the solvent was then evaporated under reduced pressure. The residue was taken up in a water/dichloromethane mixture and the organic phase was washed with water, dried over sodium sulfate and evaporated down under reduced pressure. Distillation gave 190 g (67% of theory) of E-2-(3-pyridylmethylidene)-hexanal as a yellow oil of boiling point 132°-134° C./2 mbar.

From 4.1 g (0.17 mol) of magnesium turnings which had been activated with 1 ml of 1,2-dibromomethane, a Grignard solution was prepared by the dropwise addition of a solution of 29.8 g (0.17 mol) of 4-fluorobromobenzene in 200 ml of tetrahydrofuran. Stirring was carried out for 30 minutes at 50° C., after which 20.8 g (0.11 mol) of the E-2-(3-pyridylmethylidene)-hexanal prepared above, in 100 ml of tetrahydrofuran, were added dropwise. Stirring was continued for two hours at the reflux temperature, after which the mixture was cooled, hydrolysis was carried out with water and the pH was brought to 8 with saturated NH$_4$Cl solution. The aqueous phase was extracted with ether, and the combined organic phases were washed with water, dried over Na$_2$SO$_4$ and evaporated down under reduced pressure. 27.1 g. of E-1-(4-fluorophenyl)-2-(3-pyridylmethylidene)-1-hexanol remained as a yellow oil having a purity of 94% according to gas chromatography (yield: 82% of theory; cf. Table, Example 290).

$^1$H-NMR (CDCl$_3$) δ=8.40, 8.30, 7.58, 7.22 (2-, 6-, 4-, 5-H of the pyridine moiety), 7.38, 7.02 (2 H$_m$ and 2 H$_o$ of the aryl moiety), 6.65 (C=CH), 5.30 (CHOH), 4.5 (OH), 2.20, 1.95 (3-CH$_2$), 1.23 ( 4- and 5-CH$_2$), 0.78 (6-CH$_3$). IR (film): ν=3200, 2957, 2931, 2870, 1603, 1507, 1222, 1155, 1028, 838, 713 cm$^{-1}$.

2 Preparation of E-1-(2-chlorophenyl)-2-(4-fluorophenyl)-3-(3-pyridyl)-2-propen-1-one A mixture of 24.9 g (0.10 mol) of 4-fluorobenzyl 2-chlorophenyl ketone, 10.7 g (0.10 mol) of pyridine-3-carbaldehyde and 2.9 g (0.02 mol) of piperidine acetate in 250 ml of toluene was heated under a water separator until no further water separated off. After cooling, the mixture was washed twice with saturated NaHCO$_3$ solution and with water, dried over sodium sulfate and evaporated down under reduced pressure. The residue was crystallized from 2:1 methyl tert-butyl ether/hexane. 16.6 g (40% of theory) of a product were obtained in the form of yellow crystals of melting point 102°0 C.

3. Preparation of E-1-(2-chlorophenyl)-2-(4-fluorophenyl)-3-(3-pyridyl)-2-propen-1-ol 7.6 g (0.20 mol) of sodium borohydride were added a little at a time, at 0° C., to a solution of 33.75 g (0.10 mol) of the E-1-(2-chlorophenyl)-2-(4-fluorophenyl)-3-(3-pyridyl)-2-propen-1-one, prepared under 2.), in 500 ml of methanol. Stirring was carried out for 2 hours at 0° C., excess sodium borohydride was destroyed by the dropwise addition of acetic acid and the mixture was evaporated down under reduced pressure. The residue was taken up in a water/dichloromethane mixture, and the organic phase was washed with water, dried over sodium sulfate and evaporated down under reduced pressure. Trituration with 9:1 methyl tert-butyl ether/pentane gave 27.0 g (79% of theory) of crystalline product of melting point 82°-83°C.(cf. Table, Example No. 682).

$^1$H-NMR (CDCl$_3$) δ=8.20, 8.16, 7.48, 7.27 (6-, 2-, 4-, 5-H of the pyridine moiety), 7.20-6.90 (8 aryl-H), 6 70 (C=CH), 5.90 (CHOH).

The following compounds can be prepared similarly to these Examples:

TABLE

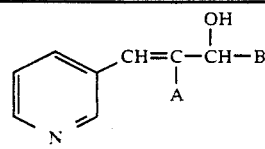

| Example No. | A | B | Phys. data (Fp, IR, $^1$H-NMR) |
|---|---|---|---|
| 1 | CH$_3$ | Phenyl | |
| 2 | CH$_3$ | 2-Methylphenyl | |
| 3 | CH$_3$ | 3-Methylphenyl | |
| 4 | CH$_3$ | 4-Methylphenyl | |
| 5 | CH$_3$ | 2,4-Dimethylphenyl | |
| 6 | CH$_3$ | 2,6-Dimethylphenyl | |
| 7 | CH$_3$ | 2,4,6-Trimethylphenyl | |
| 8 | CH$_3$ | 4-Ethylphenyl | |
| 9 | CH$_3$ | 4-Isopropylphenyl | |
| 10 | CH$_3$ | 4-tert-Butylphenyl | |
| 11 | CH$_3$ | 1-Naphthyl | |
| 12 | CH$_3$ | 2-Naphthyl | |
| 13 | CH$_3$ | 4-Biphenyl | |
| 14 | CH$_3$ | 4-(2'-Chlorobiphenyl) | |
| 15 | CH$_3$ | 4-(4'-Chlorobiphenyl) | |
| 16 | CH$_3$ | 2-Methoxyphenyl | |
| 17 | CH$_3$ | 3-Methoxyphenyl | |
| 18 | CH$_3$ | 4-Methoxyphenyl | |
| 19 | CH$_3$ | 3,4-Dimethoxyphenyl | |
| 20 | CH$_3$ | 3,4,5-Trimethoxyphenyl | |
| 21 | CH$_3$ | 4-tert-Butoxyphenyl | |
| 22 | CH$_3$ | 2-Trifluoromethylphenyl | |
| 23 | CH$_3$ | 3-Trifluoromethylphenyl | |
| 24 | CH$_3$ | 4-Trifluoromethylphenyl | |
| 25 | CH$_3$ | 4-Difluoromethoxyphenyl | |
| 26 | CH$_3$ | 4-Trifluoromethoxyphenyl | |
| 27 | CH$_3$ | 4-Tetrafluoroethoxyphenyl | |
| 28 | CH$_3$ | 2-Fluorophenyl | |
| 29 | CH$_3$ | 3-Fluorophenyl | |
| 30 | CH$_3$ | 4-Fluorophenyl | |
| 31 | CH$_3$ | 2,4-Difluorophenyl | |
| 32 | CH$_3$ | 2-Chlorophenyl | |
| 33 | CH$_3$ | 3-Chlorophenyl | |
| 34 | CH$_3$ | 4-Chlorophenyl | |
| 35 | CH$_3$ | 2,4-Dichlorophenyl | |
| 36 | CH$_3$ | 3,4-Dichlorophenyl | |
| 37 | CH$_3$ | 3,5-Dichlorophenyl | |
| 38 | CH$_3$ | 2,4,6-Trichlorophenyl | |
| 39 | CH$_3$ | 2-Chloro-4-fluorophenyl | |
| 40 | CH$_3$ | 4-Chloro-2-fluorophenyl | |
| 41 | CH$_3$ | 4-Bromophenyl | |
| 42 | CH$_3$ | Benzyl | |
| 43 | CH$_3$ | 2-Methylbenzyl | |
| 44 | CH$_3$ | 4-Methylbenzyl | |
| 45 | CH$_3$ | 2,4-Dimethylbenzyl | |
| 46 | CH$_3$ | 2-Fluorobenzyl | |
| 47 | CH$_3$ | 3-Fluorobenzyl | |
| 48 | CH$_3$ | 4-Fluorobenzyl | |
| 49 | CH$_3$ | 2-Chlorobenzyl | |
| 50 | CH$_3$ | 3-Chlorobenzyl | |
| 51 | CH$_3$ | 4-Chlorobenzyl | |
| 52 | CH$_3$ | 2,4-Dichlorobenzyl | |
| 53 | CH$_3$ | 2-Chloro-4-fluorobenzyl | |
| 54 | CH$_3$ | 2-Pyridyl | |
| 55 | CH$_3$ | 3-Pyridyl | |
| 56 | CH$_3$ | 4-Pyridyl | |
| 57 | CH$_3$ | 5-Methyl-2-pyridyl | |
| 58 | CH$_3$ | 6-Methyl-2-pyridyl | |
| 59 | CH$_3$ | 6-Chloro-3-pyridyl | |
| 60 | CH$_3$ | 5-Pyrimidinyl | |
| 61 | CH$_3$ | 2-Pyrazinyl | |
| 62 | CH$_3$ | 2-Thienyl | |
| 63 | CH$_3$ | 3-Thienyl | |
| 64 | CH$_3$ | 2-Furyl | |
| 65 | CH$_3$ | 3-Furyl | |
| 66 | C$_2$H$_5$ | Phenyl | 3219, 3084, 3060, 2967, 2874, 1452, 1046, 1026, 702 |
| 67 | C$_2$H$_5$ | 2-Methylphenyl | |
| 68 | C$_2$H$_5$ | 3-Methylphenyl | |
| 69 | C$_2$H$_5$ | 4-Methylphenyl | |
| 70 | C$_2$H$_5$ | 2,4-Dimethylphenyl | mp. 200–201° C. |
| 71 | C$_2$H$_5$ | 2,6-Dimethylphenyl | 3227, 2964, 2933, 2874, 1468, 1412, 1076, |

TABLE-continued

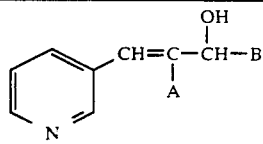

| Example No. | A | B | Phys. data (Fp. IR. $^1$H-NMR) |
|---|---|---|---|
| | | | 1027, 771, 713 |
| 72 | C$_2$H$_5$ | 2,4,6-Trimethylphenyl | mp. 178-180° C. |
| 73 | C$_2$H$_5$ | 4-Ethylphenyl | |
| 74 | C$_2$H$_5$ | 4-Isopropylphenyl | |
| 75 | C$_2$H$_5$ | 4-tert-Butylphenyl | |
| 76 | C$_2$H$_5$ | 1-Naphthyl | |
| 77 | C$_2$H$_5$ | 2-Naphthyl | |
| 78 | C$_2$H$_5$ | 4-Biphenyl | 3205, 3055, 3029, 2971, 1486, 1408, 1369, 1265, 764, 700 |
| 79 | C$_2$H$_5$ | 4-(2'-Chlorobiphenyl) | |
| 80 | C$_2$H$_5$ | 4-(4'-Chlorobiphenyl) | |
| 81 | C$_2$H$_5$ | 2-Methoxyphenyl | |
| 82 | C$_2$H$_5$ | 3-Methoxyphenyl | |
| 83 | C$_2$H$_5$ | 4-Methoxyphenyl | |
| 84 | C$_2$H$_5$ | 3,4-Dimethoxyphenyl | |
| 85 | C$_2$H$_5$ | 3,4,5-Trimethoxyphenyl | |
| 86 | C$_2$H$_5$ | 4-tert-Butoxyphenyl | |
| 87 | C$_2$H$_5$ | 2-Trifluoromethylphenyl | |
| 88 | C$_2$H$_5$ | 3-Trifluoromethylphenyl | |
| 89 | C$_2$H$_5$ | 4-Trifluoromethylphenyl | |
| 90 | C$_2$H$_5$ | 4-Difluoromethoxyphenyl | |
| 91 | C$_2$H$_5$ | 4-Trifluoromethoxyphenyl | |
| 92 | C$_2$H$_5$ | 4-Tetrafluoroethoxyphenyl | |
| 93 | C$_2$H$_5$ | 2-Fluorophenyl | |
| 94 | C$_2$H$_5$ | 3-Fluorophenyl | |
| 95 | C$_2$H$_5$ | 4-Fluorophenyl | |
| 96 | C$_2$H$_5$ | 2,4-Difluorophenyl | |
| 97 | C$_2$H$_5$ | 2-Chlorophenyl | |
| 98 | C$_2$H$_5$ | 3-Chlorophenyl | |
| 99 | C$_2$H$_5$ | 4-Chlorophenyl | mp. 185° C. |
| 100 | C$_2$H$_5$ | 2,4-Dichlorophenyl | |
| 101 | C$_2$H$_5$ | 3,4-Dichlorophenyl | |
| 102 | C$_2$H$_5$ | 3,5-Dichlorophenyl | |
| 103 | C$_2$H$_5$ | 2,4,6-Trichlorophenyl | |
| 104 | C$_2$H$_5$ | 2-Chloro-4-fluorophenyl | |
| 105 | C$_2$H$_5$ | 4-Chloro-2-fluorophenyl | |
| 106 | C$_2$H$_5$ | 4-Bromophenyl | |
| 107 | C$_2$H$_5$ | Benzyl | |
| 108 | C$_2$H$_5$ | 2-Methylbenzyl | |
| 109 | C$_2$H$_5$ | 4-Methylbenzyl | |
| 110 | C$_2$H$_5$ | 2,4-Dimethylbenzyl | |
| 111 | C$_2$H$_5$ | 2-Fluorobenzyl | |
| 112 | C$_2$H$_5$ | 3-Fluorobenzyl | |
| 113 | C$_2$H$_5$ | 4-Fluorobenzyl | |
| 114 | C$_2$H$_5$ | 2-Chlorobenzyl | |
| 115 | C$_2$H$_5$ | 3-Chlorobenzyl | |
| 116 | C$_2$H$_5$ | 4-Chlorobenzyl | |
| 117 | C$_2$H$_5$ | 2,4-Dichlorobenzyl | |
| 118 | C$_2$H$_5$ | 2-Chloro-4-fluorobenzyl | |
| 119 | C$_2$H$_5$ | 2-Pyridyl | |
| 120 | C$_2$H$_5$ | 3-Pyridyl | |
| 121 | C$_2$H$_5$ | 4-Pyridyl | |
| 122 | C$_2$H$_5$ | 5-Methyl-2-pyridyl | |
| 123 | C$_2$H$_5$ | 6-Methyl-2-pyridyl | |
| 124 | C$_2$H$_5$ | 6-Chloro-3-pyridyl | |
| 125 | C$_2$H$_5$ | 5-Pyrimidinyl | |
| 126 | C$_2$H$_5$ | 2-Pyrazinyl | |
| 127 | C$_2$H$_5$ | 2-Thienyl | |
| 128 | C$_2$H$_5$ | 3-Thienyl | |
| 129 | C$_2$H$_5$ | 2-Furyl | |
| 130 | C$_2$H$_5$ | 3-Furyl | |
| 131 | n-C$_3$H$_7$ | Phenyl | 3217, 3083, 3060, 2958, 2930, 2870, 1452, 1027, 701 |
| 132 | n-C$_3$H$_7$ | 2-Methylphenyl | 3218, 2958, 2929, 2870, 1478, 1462, 1413, 1028, 744, 713 |
| 133 | n-C$_3$H$_7$ | 3-Methylphenyl | |
| 134 | n-C$_3$H$_7$ | 4-Methylphenyl | 3219, 3023, 2958, 2928, 2869, 1454, 1413, 1043, 819, 713 |
| 135 | n-C$_3$H$_7$ | 2,4-Dimethylphenyl | 3223, 2958, 2927, 2870, 1475, 1414, 1028, 713 |
| 136 | n-C$_3$H$_7$ | 2,6-Dimethylphenyl | 3220, 2959, 2930, 2871, 1468, 1413, 1268, 1047, 1028, 771, 713 |

TABLE-continued

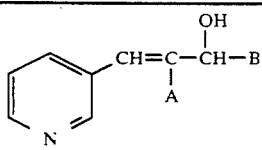

| Example No. | A | B | Phys. data (Fp, IR, ¹H-NMR) |
|---|---|---|---|
| 137 | n-$C_3H_7$ | 2,4,6-Trimethylphenyl | 3221, 2958, 2928, 2870, 1477, 1464, 1045, 1028, 851, 714 |
| 138 | n-$C_3H_7$ | 4-Ethylphenyl | |
| 139 | n-$C_3H_7$ | 4-Isopropylphenyl | |
| 140 | n-$C_3H_7$ | 4-tert-Butylphenyl | |
| 141 | n-$C_3H_7$ | 1-Naphthyl | |
| 142 | n-$C_3H_7$ | 2-Naphthyl | |
| 143 | n-$C_3H_7$ | 4-Biphenyl | 3200, 3027, 2958, 2930, 2869, 1486, 1044, 767, 746, 713, 693 |
| 144 | n-$C_3H_7$ | 4-(2'-Chlorobiphenyl) | |
| 145 | n-$C_3H_7$ | 4-(4'-Chlorobiphenyl) | |
| 146 | n-$C_3H_7$ | 2-Methoxyphenyl | |
| 147 | n-$C_3H_7$ | 3-Methoxyphenyl | |
| 148 | n-$C_3H_7$ | 4-Methoxyphenyl | |
| 149 | n-$C_3H_7$ | 3,4-Dimethoxyphenyl | |
| 150 | n-$C_3H_7$ | 3,4,5-Trimethoxyphenyl | |
| 151 | n-$C_3H_7$ | 4-tert-Butoxyphenyl | |
| 152 | n-$C_3H_7$ | 2-Trifluoromethylphenyl | |
| 153 | n-$C_3H_7$ | 3-Trifluoromethylphenyl | |
| 154 | n-$C_3H_7$ | 4-Trifluoromethylphenyl | |
| 155 | n-$C_3H_7$ | 4-Difluoromethoxyphenyl | |
| 156 | n-$C_3H_7$ | 4-Trifluoromethoxyphenyl | |
| 157 | n-$C_3H_7$ | 4-Tetrafluoroethoxyphenyl | |
| 158 | n-$C_3H_7$ | 2-Fluorophenyl | |
| 159 | n-$C_3H_7$ | 3-Fluorophenyl | |
| 160 | n-$C_3H_7$ | 4-Fluorophenyl | 2959, 2871, 1602, 1506, 1221, 1155, 1027, 838, 712 |
| 161 | n-$C_3H_7$ | 2,4-Difluorophenyl | |
| 162 | n-$C_3H_7$ | 2-Chlorophenyl | |
| 163 | n-$C_3H_7$ | 3-Chlorophenyl | |
| 164 | n-$C_3H_7$ | 4-Chlorophenyl | 3203, 2959, 2930, 2870, 1487, 1412, 1090, 1014, 828, 712 |
| 165 | n-$C_3H_7$ | 2,4-Dichlorophenyl | mp. 166–167° C. (HCl-salt) |
| 166 | n-$C_3H_7$ | 3,4-Dichlorophenyl | |
| 167 | n-$C_3H_7$ | 3,5-Dichlorophenyl | |
| 168 | n-$C_3H_7$ | 2,4,6-Trichlorophenyl | |
| 169 | n-$C_3H_7$ | 2-Chloro-4-fluorophenyl | |
| 170 | n-$C_3H_7$ | 4-Chloro-2-fluorophenyl | |
| 171 | n-$C_3H_7$ | 4-Bromophenyl | |
| 172 | n-$C_3H_7$ | Benzyl | |
| 173 | n-$C_3H_7$ | 2-Methylbenzyl | |
| 174 | n-$C_3H_7$ | 4-Methylbenzyl | |
| 175 | n-$C_3H_7$ | 2,4-Dimethylbenzyl | |
| 176 | n-$C_3H_7$ | 2-Fluorobenzyl | |
| 177 | n-$C_3H_7$ | 3-Fluorobenzyl | |
| 178 | n-$C_3H_7$ | 4-Fluorobenzyl | |
| 179 | n-$C_3H_7$ | 2-Chlorobenzyl | |
| 180 | n-$C_3H_7$ | 3-Chlorobenzyl | |
| 181 | n-$C_3H_7$ | 4-Chlorobenzyl | |
| 182 | n-$C_3H_7$ | 2,4-Dichlorobenzyl | |
| 183 | n-$C_3H_7$ | 2-Chloro-4-fluorobenzyl | |
| 184 | n-$C_3H_7$ | 2-Pyridyl | |
| 185 | n-$C_3H_7$ | 3-Pyridyl | |
| 186 | n-$C_3H_7$ | 4-Pyridyl | |
| 187 | n-$C_3H_7$ | 5-Methyl-2-pyridyl | |
| 188 | n-$C_3H_7$ | 6-Methyl-2-pyridyl | |
| 189 | n-$C_3H_7$ | 6-Chloro-3-pyridyl | |
| 190 | n-$C_3H_7$ | 5-Pyrimidinyl | |
| 191 | n-$C_3H_7$ | 2-Pyrazinyl | |
| 192 | n-$C_3H_7$ | 2-Thienyl | |
| 193 | n-$C_3H_7$ | 3-Thienyl | |
| 194 | n-$C_3H_7$ | 2-Furyl | |
| 195 | n-$C_3H_7$ | 3-Furyl | |
| 196 | iso-$C_3H_7$ | Phenyl | |
| 197 | iso-$C_3H_7$ | 2-Methylphenyl | |
| 198 | iso-$C_3H_7$ | 3-Methylphenyl | |
| 199 | iso-$C_3H_7$ | 4-Methylphenyl | |
| 200 | iso-$C_3H_7$ | 2,4-Dimethylphenyl | |
| 201 | iso-$C_3H_7$ | 2,6-Dimethylphenyl | |
| 202 | iso-$C_3H_7$ | 2,4,6-Trimethylphenyl | |
| 203 | iso-$C_3H_7$ | 4-Ethylphenyl | |
| 204 | iso-$C_3H_7$ | 4-Isopropylphenyl | |

TABLE-continued

[Structure: pyridin-3-yl-CH=C(A)-CH(OH)-B]

| Example No. | A | B | Phys. data (Fp, IR, ¹H-NMR) |
|---|---|---|---|
| 205 | iso-C₃H₇ | 4-tert-Butylphenyl | |
| 206 | iso-C₃H₇ | 1-Naphthyl | |
| 207 | iso-C₃H₇ | 2-Naphthyl | |
| 208 | iso-C₃H₇ | 4-Biphenyl | |
| 209 | iso-C₃H₇ | 4-(2'-Chlorobiphenyl) | |
| 210 | iso-C₃H₇ | 4-(4'-Chlorobiphenyl) | |
| 211 | iso-C₃H₇ | 2-Methoxyphenyl | |
| 212 | iso-C₃H₇ | 3-Methoxyphenyl | |
| 213 | iso-C₃H₇ | 4-Methoxyphenyl | |
| 214 | iso-C₃H₇ | 3,4-Dimethoxyphenyl | |
| 215 | iso-C₃H₇ | 3,4,5-Trimethoxyphenyl | |
| 216 | iso-C₃H₇ | 4-tert-Butoxyphenyl | |
| 217 | iso-C₃H₇ | 2-Trifluoromethylphenyl | |
| 218 | iso-C₃H₇ | 3-Trifluoromethylphenyl | |
| 219 | iso-C₃H₇ | 4-Trifluoromethylphenyl | |
| 220 | iso-C₃H₇ | 4-Difluoromethoxyphenyl | |
| 221 | iso-C₃H₇ | 4-Trifluoromethoxyphenyl | |
| 222 | iso-C₃H₇ | 4-Tetrafluoroethoxyphenyl | |
| 223 | iso-C₃H₇ | 2-Fluorophenyl | |
| 224 | iso-C₃H₇ | 3-Fluorophenyl | |
| 225 | iso-C₃H₇ | 4-Fluorophenyl | |
| 226 | iso-C₃H₇ | 2,4-Difluorophenyl | |
| 227 | iso-C₃H₇ | 2-Chlorophenyl | |
| 228 | iso-C₃H₇ | 3-Chlorophenyl | |
| 229 | iso-C₃H₇ | 4-Chlorophenyl | |
| 230 | iso-C₃H₇ | 2,4-Dichlorophenyl | |
| 231 | iso-C₃H₇ | 3,4-Dichlorophenyl | |
| 232 | iso-C₃H₇ | 3,5-Dichlorophenyl | |
| 233 | iso-C₃H₇ | 2,4,6-Trichlorophenyl | |
| 234 | iso-C₃H₇ | 2-Chloro-4-fluorophenyl | |
| 235 | iso-C₃H₇ | 4-Chloro-2-fluorophenyl | |
| 236 | iso-C₃H₇ | 4-Bromophenyl | |
| 237 | iso-C₃H₇ | Benzyl | |
| 238 | iso-C₃H₇ | 2-Methylbenzyl | |
| 239 | iso-C₃H₇ | 4-Methylbenzyl | |
| 240 | iso-C₃H₇ | 2,4-Dimethylbenzyl | |
| 241 | iso-C₃H₇ | 2-Fluorobenzyl | |
| 242 | iso-C₃H₇ | 3-Fluorobenzyl | |
| 243 | iso-C₃H₇ | 4-Fluorobenzyl | |
| 244 | iso-C₃H₇ | 2-Chlorobenzyl | |
| 245 | iso-C₃H₇ | 3-Chlorobenzyl | |
| 246 | iso-C₃H₇ | 4-Chlorobenzyl | |
| 247 | iso-C₃H₇ | 2,4-Dichlorobenzyl | |
| 248 | iso-C₃H₇ | 2-Chloro-4-fluorobenzyl | |
| 249 | iso-C₃H₇ | 2-Pyridyl | |
| 250 | iso-C₃H₇ | 3-Pyridyl | |
| 251 | iso-C₃H₇ | 4-Pyridyl | |
| 252 | iso-C₃H₇ | 5-Methyl-2-pyridyl | |
| 253 | iso-C₃H₇ | 6-Methyl-2-pyridyl | |
| 254 | iso-C₃H₇ | 6-Chloro-3-pyridyl | |
| 255 | iso-C₃H₇ | 5-Pyrimidinyl | |
| 256 | iso-C₃H₇ | 2-Pyrazinyl | |
| 257 | iso-C₃H₇ | 2-Thienyl | |
| 258 | iso-C₃H₇ | 3-Thienyl | |
| 259 | iso-C₃H₇ | 2-Furyl | |
| 260 | iso-C₃H₇ | 3-Furyl | |
| 261 | n-C₄H₉ | Phenyl | 3208, 3028, 2956, 2931, 2870, 1453, 1413, 1025, 702 |
| 262 | n-C₄H₉ | 2-Methylphenyl | 3234, 2955, 2929, 2870, 1478, 1461, 1027, 753, 713 |
| 263 | n-C₄H₉ | 3-Methylphenyl | |
| 264 | n-C₄H₉ | 4-Methylphenyl | 3225, 2956, 2929, 2870, 1466, 1458, 1413, 1028, 820, 714 |
| 265 | n-C₄H₉ | 2,4-Dimethylphenyl | 3226, 3031, 2956, 2928, 2870, 1476, 1458, 1413, 1027, 713 |
| 266 | n-C₄H₉ | 2,6-Dimethylphenyl | |
| 267 | n-C₄H₉ | 2,4,6-Trimethylphenyl | |
| 268 | n-C₄H₉ | 4-Ethylphenyl | |
| 269 | n-C₄H₉ | 4-Isopropylphenyl | |
| 270 | n-C₄H₉ | 4-tert-Butylphenyl | |
| 271 | n-C₄H₉ | 1-Naphthyl | |
| 272 | n-C₄H₉ | 2-Naphthyl | |

TABLE-continued

Structure: pyridin-3-yl-CH=C(A)-CH(OH)-B

| Example No. | A | B | Phys. data (Fp. IR. ¹H-NMR) |
|---|---|---|---|
| 273 | n-C₄H₉ | 4-Biphenyl | ¹H-NMR(E-Isomer) δ = 6.80(C=CH) 5.38(CHOH) |
| 274 | n-C₄H₉ | 4-(2'-Chlorobiphenyl) | |
| 275 | n-C₄H₉ | 4-(4'-Chlorobiphenyl) | |
| 276 | n-C₄H₉ | 2-Methoxyphenyl | |
| 277 | n-C₄H₉ | 3-Methoxyphenyl | |
| 278 | n-C₄H₉ | 4-Methoxyphenyl | |
| 279 | n-C₄H₉ | 3,4-Dimethoxyphenyl | |
| 280 | n-C₄H₉ | 3,4,5-Trimethoxyphenyl | |
| 281 | n-C₄H₉ | 4-tert-Butoxyphenyl | |
| 282 | n-C₄H₉ | 2-Trifluoromethylphenyl | |
| 283 | n-C₄H₉ | 3-Trifluoromethylphenyl | |
| 284 | n-C₄H₉ | 4-Trifluoromethylphenyl | |
| 285 | n-C₄H₉ | 4-Difluoromethoxyphenyl | |
| 286 | n-C₄H₉ | 4-Trifluoromethoxyphenyl | |
| 287 | n-C₄H₉ | 4-Tetrafluoroethoxyphenyl | |
| 288 | n-C₄H₉ | 2-Fluorophenyl | |
| 289 | n-C₄H₉ | 3-Fluorophenyl | |
| 290 | n-C₄H₉ | 4-Fluorophenyl | 3200, 2957, 2931, 2870, 1603, 1507, 1222, 1155, 1028, 838, 713 |
| 291 | n-C₄H₉ | 2,4-Difluorophenyl | |
| 292 | n-C₄H₉ | 2-Chlorophenyl | |
| 293 | n-C₄H₉ | 3-Chlorophenyl | |
| 294 | n-C₄H₉ | 4-Chlorophenyl | 3343, 2930, 2869, 1538, 1488, 1089, 1015, 842, 802, 685 |
| 295 | n-C₄H₉ | 2,4-Dichlorophenyl | ¹H-NMR(E-Isomer) δ = 6.58(C=CH), 5.70(CHOH) |
| 296 | n-C₄H₉ | 3,4-Dichlorophenyl | |
| 297 | n-C₄H₉ | 3,5-Dichlorophenyl | |
| 298 | n-C₄H₉ | 2,4,6-Trichlorophenyl | |
| 299 | n-C₄H₉ | 2-Chloro-4-fluorophenyl | |
| 300 | n-C₄H₉ | 4-Chloro-2-fluorophenyl | |
| 301 | n-C₄H₉ | 4-Bromophenyl | |
| 302 | n-C₄H₉ | Benzyl | |
| 303 | n-C₄H₉ | 2-Methylbenzyl | |
| 304 | n-C₄H₉ | 4-Methylbenzyl | |
| 305 | n-C₄H₉ | 2,4-Dimethylbenzyl | |
| 306 | n-C₄H₉ | 2-Fluorobenzyl | |
| 307 | n-C₄H₉ | 3-Fluorobenzyl | |
| 308 | n-C₄H₉ | 4-Fluorobenzyl | |
| 309 | n-C₄H₉ | 2-Chlorobenzyl | |
| 310 | n-C₄H₉ | 3-Chlorobenzyl | |
| 311 | n-C₄H₉ | 4-Chlorobenzyl | |
| 312 | n-C₄H₉ | 2,4-Dichlorobenzyl | |
| 313 | n-C₄H₉ | 2-Chloro-4-fluorobenzyl | |
| 314 | n-C₄H₉ | 2-Pyridyl | |
| 315 | n-C₄H₉ | 3-Pyridyl | mp. 160-162° C.(×2 HCl) |
| 316 | n-C₄H₉ | 4-Pyridyl | |
| 317 | n-C₄H₉ | 5-Methyl-2-pyridyl | |
| 318 | n-C₄H₉ | 6-Methyl-2-pyridyl | |
| 319 | n-C₄H₉ | 6-Chloro-3-pyridyl | |
| 320 | n-C₄H₉ | 5-Pyrimidinyl | |
| 321 | n-C₄H₉ | 2-Pyrazinyl | |
| 322 | n-C₄H₉ | 2-Thienyl | |
| 323 | n-C₄H₉ | 3-Thienyl | |
| 324 | n-C₄H₉ | 2-Furyl | |
| 325 | n-C₄H₉ | 3-Furyl | |
| 326 | tert.-C₄H₉ | Phenyl | 3206, 2963, 2907, 2871, 1478, 1448, 1366, 1045, 1029, 705 |
| 327 | tert.-C₄H₉ | 2-Methylphenyl | |
| 328 | tert.-C₄H₉ | 3-Methylphenyl | |
| 329 | tert.-C₄H₉ | 4-Methylphenyl | |
| 330 | tert.-C₄H₉ | 2,4-Dimethylphenyl | |
| 331 | tert.-C₄H₉ | 2,6-Dimethylphenyl | |
| 332 | tert.-C₄H₉ | 2,4,6-Trimethylphenyl | |
| 333 | tert.-C₄H₉ | 4-Ethylphenyl | |
| 334 | tert.-C₄H₉ | 4-Isopropylphenyl | |
| 335 | tert.-C₄H₉ | 4-tert-Butylphenyl | |
| 336 | tert.-C₄H₉ | 1-Naphthyl | |
| 337 | tert.-C₄H₉ | 2-Naphthyl | |
| 338 | tert.-C₄H₉ | 4-Biphenyl | |
| 339 | tert.-C₄H₉ | 4-(2'-Chlorobiphenyl) | |

TABLE-continued

Structure: 3-pyridyl-CH=C(A)-CH(OH)-B

| Example No. | A | B | Phys. data (Fp, IR, ¹H-NMR) |
|---|---|---|---|
| 340 | tert.-$C_4H_9$ | 4-(4'-Chlorobiphenyl) | |
| 341 | tert.-$C_4H_9$ | 2-Methoxyphenyl | |
| 342 | tert.-$C_4H_9$ | 3-Methoxyphenyl | |
| 343 | tert.-$C_4H_9$ | 4-Methoxyphenyl | |
| 344 | tert.-$C_4H_9$ | 3,4-Dimethoxyphenyl | |
| 345 | tert.-$C_4H_9$ | 3,4,5-Trimethoxyphenyl | |
| 346 | tert.-$C_4H_9$ | 4-tert-Butoxyphenyl | |
| 347 | tert.-$C_4H_9$ | 2-Trifluoromethylphenyl | |
| 348 | tert.-$C_4H_9$ | 3-Trifluoromethylphenyl | |
| 349 | tert.-$C_4H_9$ | 4-Trifluoromethylphenyl | |
| 350 | tert.-$C_4H_9$ | 4-Difluoromethoxyphenyl | |
| 351 | tert.-$C_4H_9$ | 4-Trifluoromethoxyphenyl | |
| 352 | tert.-$C_4H_9$ | 4-Tetrafluoroethoxyphenyl | |
| 353 | tert.-$C_4H_9$ | 2-Fluorophenyl | |
| 354 | tert.-$C_4H_9$ | 3-Fluorophenyl | |
| 355 | tert.-$C_4H_9$ | 4-Fluorophenyl | 3223, 1506, 1485, 1219, 1028, 825, 812, 714 |
| 356 | tert.-$C_4H_9$ | 2,4-Difluorophenyl | |
| 357 | tert.-$C_4H_9$ | 2-Chlorophenyl | |
| 358 | tert.-$C_4H_9$ | 3-Chlorophenyl | |
| 359 | tert.-$C_4H_9$ | 4-Chlorophenyl | 3180, 2970, 2962, 1483, 1479, 1394, 1065, 1027, 1003, 804, 750, 714 |
| 360 | tert.-$C_4H_9$ | 2,4-Dichlorophenyl | 3200, 2967, 2908, 2871, 1467, 1381, 1091, 1066, 1037, 713 |
| 361 | tert.-$C_4H_9$ | 3,4-Dichlorophenyl | |
| 362 | tert.-$C_4H_9$ | 3,5-Dichlorophenyl | |
| 363 | tert.-$C_4H_9$ | 2,4,6-Trichlorophenyl | |
| 364 | tert.-$C_4H_9$ | 2-Chloro-4-fluorophenyl | |
| 365 | tert.-$C_4H_9$ | 4-Chloro-2-fluorophenyl | |
| 366 | tert.-$C_4H_9$ | 4-Bromophenyl | |
| 367 | tert.-$C_4H_9$ | Benzyl | |
| 368 | tert.-$C_4H_9$ | 2-Methylbenzyl | |
| 369 | tert.-$C_4H_9$ | 4-Methylbenzyl | |
| 370 | tert.-$C_4H_9$ | 2,4-Dimethylbenzyl | |
| 371 | tert.-$C_4H_9$ | 2-Fluorobenzyl | |
| 372 | tert.-$C_4H_9$ | 3-Fluorobenzyl | |
| 373 | tert.-$C_4H_9$ | 4-Fluorobenzyl | |
| 374 | tert.-$C_4H_9$ | 2-Chlorobenzyl | |
| 375 | tert.-$C_4H_9$ | 3-Chlorobenzyl | |
| 376 | tert.-$C_4H_9$ | 4-Chlorobenzyl | |
| 377 | tert.-$C_4H_9$ | 2,4-Dichlorobenzyl | |
| 378 | tert.-$C_4H_9$ | 2-Chloro-4-fluorobenzyl | |
| 379 | tert.-$C_4H_9$ | 2-Pyridyl | |
| 380 | tert.-$C_4H_9$ | 3-Pyridyl | |
| 381 | tert.-$C_4H_9$ | 4-Pyridyl | |
| 382 | tert.-$C_4H_9$ | 5-Methyl-2-pyridyl | |
| 383 | tert.-$C_4H_9$ | 6-Methyl-2-pyridyl | |
| 384 | tert.-$C_4H_9$ | 6-Chloro-3-pyridyl | |
| 385 | tert.-$C_4H_9$ | 5-Pyrimidinyl | |
| 386 | tert.-$C_4H_9$ | 2-Pyrazinyl | |
| 387 | tert.-$C_4H_9$ | 2-Thienyl | |
| 388 | tert.-$C_4H_9$ | 3-Thienyl | |
| 389 | tert.-$C_4H_9$ | 2-Furyl | |
| 390 | tert.-$C_4H_9$ | 3-Furyl | |
| 391 | n-$C_5H_{11}$ | Phenyl | 3240, 2954, 2927, 2869, 1453, 1414, 1026, 701 |
| 392 | n-$C_5H_{11}$ | 2-Methylphenyl | |
| 393 | n-$C_5H_{11}$ | 3-Methylphenyl | |
| 394 | n-$C_5H_{11}$ | 4-Methylphenyl | |
| 395 | n-$C_5H_{11}$ | 2,4-Dimethylphenyl | 3240, 2954, 2927, 2927, 2869, 1466, 1457, 1414, 1028, 713 |
| 396 | n-$C_5H_{11}$ | 2,6-Dimethylphenyl | |
| 397 | n-$C_5H_{11}$ | 2,4,6-Trimethylphenyl | |
| 398 | n-$C_5H_{11}$ | 4-Ethylphenyl | |
| 399 | n-$C_5H_{11}$ | 4-Isopropylphenyl | |
| 400 | n-$C_5H_{11}$ | 4-tert-Butylphenyl | |
| 401 | n-$C_5H_{11}$ | 1-Naphthyl | |
| 402 | n-$C_5H_{11}$ | 2-Naphthyl | |
| 403 | n-$C_5H_{11}$ | 4-Biphenyl | |
| 404 | n-$C_5H_{11}$ | 4-(2'-Chlorobiphenyl) | |
| 405 | n-$C_5H_{11}$ | 4-(4'-Chlorobiphenyl) | |
| 406 | n-$C_5H_{11}$ | 2-Methoxyphenyl | |

TABLE-continued

Structure: pyridin-3-yl–CH=C(A)–CH(OH)–B

| Example No. | A | B | Phys. data (Fp, IR, $^1$H-NMR) |
|---|---|---|---|
| 407 | n-C$_5$H$_{11}$ | 3-Methoxyphenyl | |
| 408 | n-C$_5$H$_{11}$ | 4-Methoxyphenyl | |
| 409 | n-C$_5$H$_{11}$ | 3,4-Dimethoxyphenyl | |
| 410 | n-C$_5$H$_{11}$ | 3,4,5-Trimethoxyphenyl | |
| 411 | n-C$_5$H$_{11}$ | 4-tert-Butoxyphenyl | |
| 412 | n-C$_5$H$_{11}$ | 2-Trifluoromethylphenyl | |
| 413 | n-C$_5$H$_{11}$ | 3-Trifluoromethylphenyl | |
| 414 | n-C$_5$H$_{11}$ | 4-Trifluoromethylphenyl | |
| 415 | n-C$_5$H$_{11}$ | 4-Difluoromethoxyphenyl | |
| 416 | n-C$_5$H$_{11}$ | 4-Trifluoromethoxyphenyl | |
| 417 | n-C$_5$H$_{11}$ | 4-Tetrafluoroethoxyphenyl | |
| 418 | n-C$_5$H$_{11}$ | 2-Fluorophenyl | |
| 419 | n-C$_5$H$_{11}$ | 3-Fluorophenyl | |
| 420 | n-C$_5$H$_{11}$ | 4-Fluorophenyl | 3200, 2955, 2930, 2869, 1603, 1507, 1227 1155, 838, 713 |
| 421 | n-C$_5$H$_{11}$ | 2,4-Difluorophenyl | |
| 422 | n-C$_5$H$_{11}$ | 2-Chlorophenyl | |
| 423 | n-C$_5$H$_{11}$ | 3-Chlorophenyl | |
| 424 | n-C$_5$H$_{11}$ | 4-Chlorophenyl | 3208, 2955, 2929, 2869, 1488, 1090, 1015, 827, 712 |
| 425 | n-C$_5$H$_{11}$ | 2,4-Dichlorophenyl | mp. 153–155° C. (×HCl) |
| 426 | n-C$_5$H$_{11}$ | 3,4-Dichlorophenyl | |
| 427 | n-C$_5$H$_{11}$ | 3,5-Dichlorophenyl | |
| 428 | n-C$_5$H$_{11}$ | 2,4,6-Trichlorophenyl | |
| 429 | n-C$_5$H$_{11}$ | 2-Chloro-4-fluorophenyl | |
| 430 | n-C$_5$H$_{11}$ | 4-Chloro-2-fluorophenyl | |
| 431 | n-C$_5$H$_{11}$ | 4-Bromophenyl | |
| 432 | n-C$_5$H$_{11}$ | Benzyl | |
| 433 | n-C$_5$H$_{11}$ | 2-Methylbenzyl | |
| 434 | n-C$_5$H$_{11}$ | 4-Methylbenzyl | |
| 435 | n-C$_5$H$_{11}$ | 2,4-Dimethylbenzyl | |
| 436 | n-C$_5$H$_{11}$ | 2-Fluorobenzyl | |
| 437 | n-C$_5$H$_{11}$ | 3-Fluorobenzyl | |
| 438 | n-C$_5$H$_{11}$ | 4-Fluorobenzyl | |
| 439 | n-C$_5$H$_{11}$ | 2-Chlorobenzyl | |
| 440 | n-C$_5$H$_{11}$ | 3-Chlorobenzyl | |
| 441 | n-C$_5$H$_{11}$ | 4-Chlorobenzyl | |
| 442 | n-C$_5$H$_{11}$ | 2,4-Dichlorobenzyl | |
| 443 | n-C$_5$H$_{11}$ | 2-Chloro-4-fluorobenzyl | |
| 444 | n-C$_5$H$_{11}$ | 2-Pyridyl | |
| 445 | n-C$_5$H$_{11}$ | 3-Pyridyl | |
| 446 | n-C$_5$H$_{11}$ | 4-Pyridyl | |
| 447 | n-C$_5$H$_{11}$ | 5-Methyl-2-pyridyl | |
| 448 | n-C$_5$H$_{11}$ | 6-Methyl-2-pyridyl | |
| 449 | n-C$_5$H$_{11}$ | 6-Chloro-3-pyridyl | |
| 450 | n-C$_5$H$_{11}$ | 5-Pyrimidinyl | |
| 451 | n-C$_5$H$_{11}$ | 2-Pyrazinyl | |
| 452 | n-C$_5$H$_{11}$ | 2-Thienyl | |
| 453 | n-C$_5$H$_{11}$ | 3-Thienyl | |
| 454 | n-C$_5$H$_{11}$ | 2-Furyl | |
| 455 | n-C$_5$H$_{11}$ | 3-Furyl | |
| 456 | neo-C$_5$H$_{11}$ | Phenyl | $^1$H-NMR: E-Isomer: δ = 7.05 (C=CH), 5.38 (CHOH), 2.58, 1.63, 0.80 (CH$_2$C(CH$_3$)$_3$). Z-Isomer: δ = 6.62 (C=CH), 5.70(CHOH), 2.10, 1.98, 0.98 (CH$_2$C(CH$_3$)$_3$). |
| 457 | neo-C$_5$H$_{11}$ | 2-Methylphenyl | 2952, 2864, 1476, 1464, 1364, 1046, 1028, 760, 728, 715 |
| 458 | neo-C$_5$H$_{11}$ | 3-Methylphenyl | |
| 459 | neo-C$_5$H$_{11}$ | 4-Methylphenyl | mp. 154–156° C. (×HCl) |
| 460 | neo-C$_5$H$_{11}$ | 2,4-Dimethylphenyl | 3227, 2951, 2864, 1476, 1467, 1412, 1363, 1045, 1028, 715 |
| 461 | neo-C$_5$H$_{11}$ | 2,6-Dimethylphenyl | |
| 462 | neo-C$_5$H$_{11}$ | 2,4,6-Trimethylphenyl | |
| 463 | neo-C$_5$H$_{11}$ | 4-Ethylphenyl | |
| 464 | neo-C$_5$H$_{11}$ | 4-Isopropylphenyl | |
| 465 | neo-C$_5$H$_{11}$ | 4-tert-Butylphenyl | |
| 466 | neo-C$_5$H$_{11}$ | 1-Naphthyl | |
| 467 | neo-C$_5$H$_{11}$ | 2-Naphthyl | |
| 468 | neo-C$_5$H$_{11}$ | 4-Biphenyl | |
| 469 | neo-C$_5$H$_{11}$ | 4-(2'-Chlorobiphenyl) | |
| 470 | neo-C$_5$H$_{11}$ | 4-(4'-Chlorobiphenyl) | |

TABLE-continued

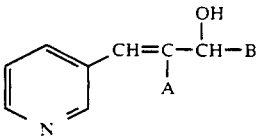

| Example No. | A | B | Phys. data (Fp. IR. $^1$H-NMR) |
|---|---|---|---|
| 471 | neo-$C_5H_{11}$ | 2-Methoxyphenyl | |
| 472 | neo-$C_5H_{11}$ | 3-Methoxyphenyl | |
| 473 | neo-$C_5H_{11}$ | 4-Methoxyphenyl | |
| 474 | neo-$C_5H_{11}$ | 3,4-Dimethoxyphenyl | |
| 475 | neo-$C_5H_{11}$ | 3,4,5-Trimethoxyphenyl | |
| 476 | neo-$C_5H_{11}$ | 4-tert-Butoxyphenyl | |
| 477 | neo-$C_5H_{11}$ | 2-Trifluoromethylphenyl | |
| 478 | neo-$C_5H_{11}$ | 3-Trifluoromethylphenyl | |
| 479 | neo-$C_5H_{11}$ | 4-Trifluoromethylphenyl | |
| 480 | neo-$C_5H_{11}$ | 4-Difluoromethoxyphenyl | |
| 481 | neo-$C_5H_{11}$ | 4-Trifluoromethoxyphenyl | |
| 482 | neo-$C_5H_{11}$ | 4-Tetrafluoroethoxyphenyl | |
| 483 | neo-$C_5H_{11}$ | 2-Fluorophenyl | |
| 484 | neo-$C_5H_{11}$ | 3-Fluorophenyl | |
| 485 | neo-$C_5H_{11}$ | 4-Fluorophenyl | $^1$H-NMR: E-Isomer: δ = 7.00 (C=CH) 5.38 (CHOH), 0.78 (CMe$_3$). Z-Isomer: δ = 6.60 (C=CH), 5.65 (CHOH), 0.97 (CMe$_3$) |
| 486 | neo-$C_5H_{11}$ | 2,4-Difluorophenyl | |
| 487 | neo-$C_5H_{11}$ | 2-Chlorophenyl | |
| 488 | neo-$C_5H_{11}$ | 3-Chlorophenyl | |
| 489 | neo-$C_5H_{11}$ | 4-Chlorophenyl | $^1$H-NMR: E-Isomer: δ = 7.00 (C=CH) 5.35 (CHOH), 2.55, 1.63, 0.78 (CH$_2$CMe$_3$). Z-Isomer: δ = 6.58 (C=CH), 5.62 (CHOH), 2.08, 1.95, 0.98 (CH$_2$CMe$_3$) |
| 490 | neo-$C_5H_{11}$ | 2,4-Dichlorophenyl | mp. 120° C. (Zers.) (×HCl) |
| 491 | neo-$C_5H_{11}$ | 3,4-Dichlorophenyl | |
| 492 | neo-$C_5H_{11}$ | 3,5-Dichlorophenyl | |
| 493 | neo-$C_5H_{11}$ | 2,4,6-Trichlorophenyl | |
| 494 | neo-$C_5H_{11}$ | 2-Chloro-4-fluorophenyl | |
| 495 | neo-$C_5H_{11}$ | 4-Chloro-2-fluorophenyl | |
| 496 | neo-$C_5H_{11}$ | 4-Bromophenyl | |
| 497 | neo-$C_5H_{11}$ | Benzyl | |
| 498 | neo-$C_5H_{11}$ | 2-Methylbenzyl | |
| 499 | neo-$C_5H_{11}$ | 4-Methylbenzyl | |
| 500 | neo-$C_5H_{11}$ | 2,4-Dimethylbenzyl | |
| 501 | neo-$C_5H_{11}$ | 2-Fluorobenzyl | |
| 502 | neo-$C_5H_{11}$ | 3-Fluorobenzyl | |
| 503 | neo-$C_5H_{11}$ | 4-Fluorobenzyl | |
| 504 | neo-$C_5H_{11}$ | 2-Chlorobenzyl | |
| 505 | neo-$C_5H_{11}$ | 3-Chlorobenzyl | |
| 506 | neo-$C_5H_{11}$ | 4-Chlorobenzyl | |
| 507 | neo-$C_5H_{11}$ | 2,4-Dichlorobenzyl | |
| 508 | neo-$C_5H_{11}$ | 2-Chloro-4-fluorobenzyl | |
| 509 | neo-$C_5H_{11}$ | 2-Pyridyl | |
| 510 | neo-$C_5H_{11}$ | 3-Pyridyl | |
| 511 | neo-$C_5H_{11}$ | 4-Pyridyl | |
| 512 | neo-$C_5H_{11}$ | 5-Methyl-2-pyridyl | |
| 513 | neo-$C_5H_{11}$ | 6-Methyl-2-pyridyl | |
| 514 | neo-$C_5H_{11}$ | 6-Chloro-3-pyridyl | |
| 515 | neo-$C_5H_{11}$ | 5-Pyrimidinyl | |
| 516 | neo-$C_5H_{11}$ | 2-Pyrazinyl | |
| 517 | neo-$C_5H_{11}$ | 2-Thienyl | |
| 518 | neo-$C_5H_{11}$ | 3-Thienyl | |
| 519 | neo-$C_5H_{11}$ | 2-Furyl | |
| 520 | neo-$C_5H_{11}$ | 3-Furyl | |
| 521 | n-$C_6H_{13}$ | Phenyl | 3219, 2954, 2927, 2856, 1467, 1453, 1045, 1026, 713, 701 |
| 522 | n-$C_6H_{13}$ | 2-Methylphenyl | |
| 523 | n-$C_6H_{13}$ | 3-Methylphenyl | |
| 524 | n-$C_6H_{13}$ | 4-Methylphenyl | |
| 525 | n-$C_6H_{13}$ | 2,4-Dimethylphenyl | |
| 526 | n-$C_6H_{13}$ | 2,6-Dimethylphenyl | |
| 527 | n-$C_6H_{13}$ | 2,4,6-Trimethylphenyl | |
| 528 | n-$C_6H_{13}$ | 4-Ethylphenyl | |
| 529 | n-$C_6H_{13}$ | 4-Isopropylphenyl | |
| 530 | n-$C_6H_{13}$ | 4-tert-Butylphenyl | |
| 531 | n-$C_6H_{13}$ | 1-Naphthyl | |
| 532 | n-$C_6H_{13}$ | 2-Naphthyl | |
| 533 | n-$C_6H_{13}$ | 4-Biphenyl | |
| 534 | n-$C_6H_{13}$ | 4-(2'-Chlorobiphenyl) | |
| 535 | n-$C_6H_{13}$ | 4-(4'-Chlorobiphenyl) | |

TABLE-continued

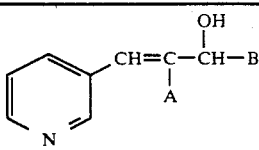

| Example No. | A | B | Phys. data (Fp, IR, ¹H-NMR) |
|---|---|---|---|
| 536 | n-$C_6H_{13}$ | 2-Methoxyphenyl | |
| 537 | n-$C_6H_{13}$ | 3-Methoxyphenyl | |
| 538 | n-$C_6H_{13}$ | 4-Methoxyphenyl | |
| 539 | n-$C_6H_{13}$ | 3,4-Dimethoxyphenyl | |
| 540 | n-$C_6H_{13}$ | 3,4,5-Trimethoxyphenyl | |
| 541 | n-$C_6H_{13}$ | 4-tert-Butoxyphenyl | |
| 542 | n-$C_6H_{13}$ | 2-Trifluoromethylphenyl | |
| 543 | n-$C_6H_{13}$ | 3-Trifluoromethylphenyl | |
| 544 | n-$C_6H_{13}$ | 4-Trifluoromethylphenyl | |
| 545 | n-$C_6H_{13}$ | 4-Difluoromethoxyphenyl | |
| 546 | n-$C_6H_{13}$ | 4-Trifluoromethoxyphenyl | |
| 547 | n-$C_6H_{13}$ | 4-Tetrafluoroethoxyphenyl | |
| 548 | n-$C_6H_{13}$ | 2-Fluorophenyl | |
| 549 | n-$C_6H_{13}$ | 3-Fluorophenyl | |
| 550 | n-$C_6H_{13}$ | 4-Fluorophenyl | 3200, 2955, 2929, 2857, 1507, 1222, 1155 838, 713 |
| 551 | n-$C_6H_{13}$ | 2,4-Difluorophenyl | |
| 552 | n-$C_6H_{13}$ | 2-Chlorophenyl | |
| 553 | n-$C_6H_{13}$ | 3-Chlorophenyl | |
| 554 | n-$C_6H_{13}$ | 4-Chlorophenyl | 3200, 2955, 2928, 2869, 2856, 1488, 1091, 1051, 829, 712 |
| 555 | n-$C_6H_{13}$ | 2,4-Dichlorophenyl | 3260, 2953, 2928, 2856, 1587, 1572, 1560, 1468, 1414, 1312, 715 |
| 556 | n-$C_6H_{13}$ | 3,4-Dichlorophenyl | |
| 557 | n-$C_6H_{13}$ | 3,5-Dichlorophenyl | |
| 558 | n-$C_6H_{13}$ | 2,4,6-Trichlorophenyl | |
| 559 | n-$C_6H_{13}$ | 2-Chloro-4-fluorophenyl | |
| 560 | n-$C_6H_{13}$ | 4-Chloro-2-fluorophenyl | |
| 561 | n-$C_6H_{13}$ | 4-Bromophenyl | |
| 562 | n-$C_6H_{13}$ | Benzyl | |
| 563 | n-$C_6H_{13}$ | 2-Methylbenzyl | |
| 564 | n-$C_6H_{13}$ | 4-Methylbenzyl | |
| 565 | n-$C_6H_{13}$ | 2,4-Dimethylbenzyl | |
| 566 | n-$C_6H_{13}$ | 2-Fluorobenzyl | |
| 567 | n-$C_6H_{13}$ | 3-Fluorobenzyl | |
| 568 | n-$C_6H_{13}$ | 4-Fluorobenzyl | |
| 569 | n-$C_6H_{13}$ | 2-Chlorobenzyl | |
| 570 | n-$C_6H_{13}$ | 3-Chlorobenzyl | |
| 571 | n-$C_6H_{13}$ | 4-Chlorobenzyl | |
| 572 | n-$C_6H_{13}$ | 2,4-Dichlorobenzyl | |
| 573 | n-$C_6H_{13}$ | 2-Chloro-4-fluorobenzyl | |
| 574 | n-$C_6H_{13}$ | 2-Pyridyl | |
| 575 | n-$C_6H_{13}$ | 3-Pyridyl | |
| 576 | n-$C_6H_{13}$ | 4-Pyridyl | |
| 577 | n-$C_6H_{13}$ | 5-Methyl-2-pyridyl | |
| 578 | n-$C_6H_{13}$ | 6-Methyl-2-pyridyl | |
| 579 | n-$C_6H_{13}$ | 6-Chloro-3-pyridyl | |
| 580 | n-$C_6H_{13}$ | 5-Pyrimidinyl | |
| 581 | n-$C_6H_{13}$ | 2-Pyrazinyl | |
| 582 | n-$C_6H_{13}$ | 2-Thienyl | |
| 583 | n-$C_6H_{13}$ | 3-Thienyl | |
| 584 | n-$C_6H_{13}$ | 2-Furyl | |
| 585 | n-$C_6H_{13}$ | 3-Furyl | |
| 586 | Phenyl | Phenyl | mp. 149° C. |
| 587 | Phenyl | 2-Methylphenyl | |
| 588 | Phenyl | 3-Methylphenyl | |
| 589 | Phenyl | 4-Methylphenyl | |
| 590 | Phenyl | 2,4-Dimethylphenyl | |
| 591 | Phenyl | 2,6-Dimethylphenyl | |
| 592 | Phenyl | 2,4,6-Trimethylphenyl | |
| 593 | Phenyl | 4-Ethylphenyl | |
| 594 | Phenyl | 4-Isopropylphenyl | |
| 595 | Phenyl | 4-tert-Butylphenyl | |
| 596 | Phenyl | 1-Naphthyl | |
| 597 | Phenyl | 2-Naphthyl | |
| 598 | Phenyl | 4-Biphenyl | |
| 599 | Phenyl | 4-(2'-Chlorobiphenyl) | |
| 600 | Phenyl | 4-(4'-Chlorobiphenyl) | |
| 601 | Phenyl | 2-Methoxyphenyl | |
| 602 | Phenyl | 3-Methoxyphenyl | |
| 603 | Phenyl | 4-Methoxyphenyl | |
| 604 | Phenyl | 3,4-Dimethoxyphenyl | |

TABLE-continued

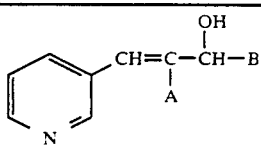

| Example No. | A | B | Phys. data (Fp. IR. $^1$H-NMR) |
|---|---|---|---|
| 605 | Phenyl | 3,4,5-Trimethoxyphenyl | |
| 606 | Phenyl | 4-tert-Butoxyphenyl | |
| 607 | Phenyl | 2-Trifluoromethylphenyl | |
| 608 | Phenyl | 3-Trifluoromethylphenyl | |
| 609 | Phenyl | 4-Trifluoromethylphenyl | |
| 610 | Phenyl | 4-Difluoromethoxyphenyl | |
| 611 | Phenyl | 4-Trifluoromethoxyphenyl | |
| 612 | Phenyl | 4-Tetrafluoroethoxyphenyl | |
| 613 | Phenyl | 2-Fluorophenyl | |
| 614 | Phenyl | 3-Fluorophenyl | |
| 615 | Phenyl | 4-Fluorophenyl | |
| 616 | Phenyl | 2,4-Difluorophenyl | |
| 617 | Phenyl | 2-Chlorophenyl | |
| 618 | Phenyl | 3-Chlorophenyl | |
| 619 | Phenyl | 4-Chlorophenyl | mp. 89° C. |
| 620 | Phenyl | 2,4-Dichlorophenyl | |
| 621 | Phenyl | 3,4-Dichlorophenyl | |
| 622 | Phenyl | 3,5-Dichlorophenyl | |
| 623 | Phenyl | 2,4,6-Trichlorophenyl | |
| 624 | Phenyl | 2-Chloro-4-fluorophenyl | |
| 625 | Phenyl | 4-Chloro-2-fluorophenyl | |
| 626 | Phenyl | 4-Bromophenyl | |
| 627 | Phenyl | Benzyl | |
| 628 | Phenyl | 2-Methylbenzyl | |
| 629 | Phenyl | 4-Methylbenzyl | |
| 630 | Phenyl | 2,4-Dimethylbenzyl | |
| 631 | Phenyl | 2-Fluorobenzyl | |
| 632 | Phenyl | 3-Fluorobenzyl | |
| 633 | Phenyl | 4-Fluorobenzyl | |
| 634 | Phenyl | 2-Chlorobenzyl | |
| 635 | Phenyl | 3-Chlorobenzyl | |
| 636 | Phenyl | 4-Chlorobenzyl | |
| 637 | Phenyl | 2,4-Dichlorobenzyl | |
| 638 | Phenyl | 2-Chloro-4-fluorobenzyl | |
| 639 | Phenyl | 2-Pyridyl | |
| 640 | Phenyl | 3-Pyridyl | |
| 641 | Phenyl | 4-Pyridyl | |
| 642 | Phenyl | 5-Methyl-2-pyridyl | |
| 643 | Phenyl | 6-Methyl-2-pyridyl | |
| 644 | Phenyl | 6-Chloro-3-pyridyl | |
| 645 | Phenyl | 5-Pyrimidinyl | |
| 646 | Phenyl | 2-Pyrazinyl | |
| 647 | Phenyl | 2-Thienyl | |
| 648 | Phenyl | 3-Thienyl | |
| 649 | Phenyl | 2-Furyl | |
| 650 | Phenyl | 3-Furyl | |
| 651 | 4-Fluorophenyl | Phenyl | mp. 96° C. |
| 652 | 4-Fluorophenyl | 2-Methylphenyl | |
| 653 | 4-Fluorophenyl | 3-Methylphenyl | |
| 654 | 4-Fluorophenyl | 4-Methylphenyl | |
| 655 | 4-Fluorophenyl | 2,4-Dimethylphenyl | |
| 656 | 4-Fluorophenyl | 2,6-Dimethylphenyl | |
| 657 | 4-Fluorophenyl | 2,4,6-Trimethylphenyl | |
| 658 | 4-Fluorophenyl | 4-Ethylphenyl | |
| 659 | 4-Fluorophenyl | 4-Isopropylphenyl | |
| 660 | 4-Fluorophenyl | 4-tert-Butylphenyl | |
| 661 | 4-Fluorophenyl | 1-Naphthyl | |
| 662 | 4-Fluorophenyl | 2-Naphthyl | |
| 663 | 4-Fluorophenyl | 4-Biphenyl | |
| 664 | 4-Fluorophenyl | 4-(2'-Chlorobiphenyl) | |
| 665 | 4-Fluorophenyl | 4-(4'-Chlorobiphenyl) | |
| 666 | 4-Fluorophenyl | 2-Methoxyphenyl | |
| 667 | 4-Fluorophenyl | 3-Methoxyphenyl | |
| 668 | 4-Fluorophenyl | 4-Methoxyphenyl | |
| 669 | 4-Fluorophenyl | 3,4-Dimethoxyphenyl | |
| 670 | 4-Fluorophenyl | 3,4,5-Trimethoxyphenyl | |
| 671 | 4-Fluorophenyl | 4-tert-Butoxyphenyl | |
| 672 | 4-Fluorophenyl | 2-Trifluoromethylphenyl | |
| 673 | 4-Fluorophenyl | 3-Trifluoromethylphenyl | |
| 674 | 4-Fluorophenyl | 4-Trifluoromethylphenyl | |
| 675 | 4-Fluorophenyl | 4-Difluoromethoxyphenyl | |
| 676 | 4-Fluorophenyl | 4-Trifluoromethoxyphenyl | |

TABLE-continued

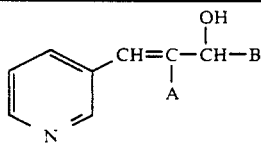

| Example No. | A | B | Phys. data (Fp, IR, ¹H-NMR) |
|---|---|---|---|
| 677 | 4-Fluorophenyl | 4-Tetrafluoroethoxyphenyl | |
| 678 | 4-Fluorophenyl | 2-Fluorophenyl | |
| 679 | 4-Fluorophenyl | 3-Fluorophenyl | |
| 680 | 4-Fluorophenyl | 4-Fluorophenyl | |
| 681 | 4-Fluorophenyl | 2,4-Difluorophenyl | |
| 682 | 4-Fluorophenyl | 2-Chlorophenyl | mp. 82–83° C. |
| 683 | 4-Fluorophenyl | 3-Chlorophenyl | |
| 684 | 4-Fluorophenyl | 4-Chlorophenyl | mp. 104° C. |
| 685 | 4-Fluorophenyl | 2,4-Dichlorophenyl | |
| 686 | 4-Fluorophenyl | 3,4-Dichlorophenyl | |
| 687 | 4-Fluorophenyl | 3,5-Dichlorophenyl | |
| 688 | 4-Fluorophenyl | 2,4,6-Trichlorophenyl | |
| 689 | 4-Fluorophenyl | 2-Chloro-4-fluorophenyl | |
| 690 | 4-Fluorophenyl | 4-Chloro-2-fluorophenyl | |
| 691 | 4-Fluorophenyl | 4-Bromophenyl | |
| 692 | 4-Fluorophenyl | Benzyl | |
| 693 | 4-Fluorophenyl | 2-Methylbenzyl | |
| 694 | 4-Fluorophenyl | 4-Methylbenzyl | |
| 695 | 4-Fluorophenyl | 2,4-Dimethylbenzyl | |
| 696 | 4-Fluorophenyl | 2-Fluorobenzyl | |
| 697 | 4-Fluorophenyl | 3-Fluorobenzyl | |
| 698 | 4-Fluorophenyl | 4-Fluorobenzyl | |
| 699 | 4-Fluorophenyl | 2-Chlorobenzyl | |
| 700 | 4-Fluorophenyl | 3-Chlorobenzyl | |
| 701 | 4-Fluorophenyl | 4-Chlorobenzyl | |
| 702 | 4-Fluorophenyl | 2,4-Dichlorobenzyl | |
| 703 | 4-Fluorophenyl | 2-Chloro-4-fluorobenzyl | |
| 704 | 4-Fluorophenyl | 2-Pyridyl | |
| 705 | 4-Fluorophenyl | 3-Pyridyl | |
| 706 | 4-Fluorophenyl | 4-Pyridyl | |
| 707 | 4-Fluorophenyl | 5-Methyl-2-pyridyl | |
| 708 | 4-Fluorophenyl | 6-Methyl-2-pyridyl | |
| 709 | 4-Fluorophenyl | 6-Chloro-3-pyridyl | |
| 710 | 4-Fluorophenyl | 5-Pyrimidinyl | |
| 711 | 4-Fluorophenyl | 2-Pyrazinyl | |
| 712 | 4-Fluorophenyl | 2-Thienyl | |
| 713 | 4-Fluorophenyl | 3-Thienyl | |
| 714 | 4-Fluorophenyl | 2-Furyl | |
| 715 | 4-Fluorophenyl | 3-Furyl | |
| 716 | 4-Chlorophenyl | Phenyl | |
| 717 | 4-Chlorophenyl | 2-Methylphenyl | |
| 718 | 4-Chlorophenyl | 3-Methylphenyl | |
| 719 | 4-Chlorophenyl | 4-Methylphenyl | |
| 720 | 4-Chlorophenyl | 2,4-Dimethylphenyl | |
| 721 | 4-Chlorophenyl | 2,6-Dimethylphenyl | |
| 722 | 4-Chlorophenyl | 2,4,6-Trimethylphenyl | |
| 723 | 4-Chlorophenyl | 4-Ethylphenyl | |
| 724 | 4-Chlorophenyl | 4-Isopropylphenyl | |
| 725 | 4-Chlorophenyl | 4-tert-Butylphenyl | |
| 726 | 4-Chlorophenyl | 1-Naphthyl | |
| 727 | 4-Chlorophenyl | 2-Naphthyl | |
| 728 | 4-Chlorophenyl | 4-Biphenyl | |
| 729 | 4-Chlorophenyl | 4-(2'-Chlorobiphenyl) | |
| 730 | 4-Chlorophenyl | 4-(4'-Chlorobiphenyl) | |
| 731 | 4-Chlorophenyl | 2-Methoxyphenyl | |
| 732 | 4-Chlorophenyl | 3-Methoxyphenyl | |
| 733 | 4-Chlorophenyl | 4-Methoxyphenyl | |
| 734 | 4-Chlorophenyl | 3,4-Dimethoxyphenyl | |
| 735 | 4-Chlorophenyl | 3,4,5-Trimethoxyphenyl | |
| 736 | 4-Chlorophenyl | 4-tert-Butoxyphenyl | |
| 737 | 4-Chlorophenyl | 2-Trifluoromethylphenyl | |
| 738 | 4-Chlorophenyl | 3-Trifluoromethylphenyl | |
| 739 | 4-Chlorophenyl | 4-Trifluoromethylphenyl | |
| 740 | 4-Chlorophenyl | 4-Difluoromethoxyphenyl | |
| 741 | 4-Chlorophenyl | 4-Trifluoromethoxyphenyl | |
| 742 | 4-Chlorophenyl | 4-Tetrafluoroethoxyphenyl | |
| 743 | 4-Chlorophenyl | 2-Fluorophenyl | |
| 744 | 4-Chlorophenyl | 3-Fluorophenyl | |
| 745 | 4-Chlorophenyl | 4-Fluorophenyl | |
| 746 | 4-Chlorophenyl | 2,4-Difluorophenyl | |
| 747 | 4-Chlorophenyl | 2-Chlorophenyl | |
| 748 | 4-Chlorophenyl | 3-Chlorophenyl | |

TABLE-continued

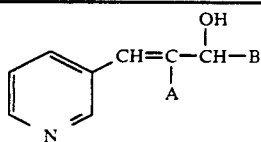

| Example No. | A | B | Phys. data (Fp, IR, $^1$H-NMR) |
|---|---|---|---|
| 749 | 4-Chlorophenyl | 4-Chlorophenyl | |
| 750 | 4-Chlorophenyl | 2,4-Dichlorophenyl | |
| 751 | 4-Chlorophenyl | 3,4-Dichlorophenyl | |
| 752 | 4-Chlorophenyl | 3,5-Dichlorophenyl | |
| 753 | 4-Chlorophenyl | 2,4,6-Trichlorophenyl | |
| 754 | 4-Chlorophenyl | 2-Chloro-4-fluorophenyl | |
| 755 | 4-Chlorophenyl | 4-Chloro-2-fluorophenyl | |
| 756 | 4-Chlorophenyl | 4-Bromophenyl | |
| 757 | 4-Chlorophenyl | Benzyl | |
| 758 | 4-Chlorophenyl | 2-Methylbenzyl | |
| 759 | 4-Chlorophenyl | 4-Methylbenzyl | |
| 760 | 4-Chlorophenyl | 2,4-Dimethylbenzyl | |
| 761 | 4-Chlorophenyl | 2-Fluorobenzyl | |
| 762 | 4-Chlorophenyl | 3-Fluorobenzyl | |
| 763 | 4-Chlorophenyl | 4-Fluorobenzyl | |
| 764 | 4-Chlorophenyl | 2-Chlorobenzyl | |
| 765 | 4-Chlorophenyl | 3-Chlorobenzyl | |
| 766 | 4-Chlorophenyl | 4-Chlorobenzyl | |
| 767 | 4-Chlorophenyl | 2,4-Dichlorobenzyl | |
| 768 | 4-Chlorophenyl | 2-Chloro-4-fluorobenzyl | |
| 769 | 4-Chlorophenyl | 2-Pyridyl | |
| 770 | 4-Chlorophenyl | 3-Pyridyl | |
| 771 | 4-Chlorophenyl | 4-Pyridyl | |
| 772 | 4-Chlorophenyl | 5-Methyl-2-pyridyl | |
| 773 | 4-Chlorophenyl | 6-Methyl-2-pyridyl | |
| 774 | 4-Chlorophenyl | 6-Chloro-3-pyridyl | |
| 775 | 4-Chlorophenyl | 5-Pyrimidinyl | |
| 776 | 4-Chlorophenyl | 2-Pyrazinyl | |
| 777 | 4-Chlorophenyl | 2-Thienyl | |
| 778 | 4-Chlorophenyl | 3-Thienyl | |
| 779 | 4-Chlorophenyl | 2-Furyl | |
| 780 | 4-Chlorophenyl | 3-Furyl | |
| 781 | 2,4-Dichlorophenyl | Phenyl | |
| 782 | 2,4-Dichlorophenyl | 2-Methylphenyl | |
| 783 | 2,4-Dichlorophenyl | 3-Methylphenyl | |
| 784 | 2,4-Dichlorophenyl | 4-Methylphenyl | |
| 785 | 2,4-Dichlorophenyl | 2,4-Dimethylphenyl | |
| 786 | 2,4-Dichlorophenyl | 2,6-Dimethylphenyl | |
| 787 | 2,4-Dichlorophenyl | 2,4,6-Trimethylphenyl | |
| 788 | 2,4-Dichlorophenyl | 4-Ethylphenyl | |
| 789 | 2,4-Dichlorophenyl | 4-Isopropylphenyl | |
| 790 | 2,4-Dichlorophenyl | 4-tert-Butylphenyl | |
| 791 | 2,4-Dichlorophenyl | 1-Naphthyl | |
| 792 | 2,4-Dichlorophenyl | 2-Naphthyl | |
| 793 | 2,4-Dichlorophenyl | 4-Biphenyl | |
| 794 | 2,4-Dichlorophenyl | 4-(2'-Chlorobiphenyl) | |
| 795 | 2,4-Dichlorophenyl | 4-(4'-Chlorobiphenyl) | |
| 796 | 2,4-Dichlorophenyl | 2-Methoxyphenyl | |
| 797 | 2,4-Dichlorophenyl | 3-Methoxyphenyl | |
| 798 | 2,4-Dichlorophenyl | 4-Methoxyphenyl | |
| 799 | 2,4-Dichlorophenyl | 3,4-Dimethoxyphenyl | |
| 800 | 2,4-Dichlorophenyl | 3,4,5-Trimethoxyphenyl | |
| 801 | 2,4-Dichlorophenyl | 4-tert-Butoxyphenyl | |
| 802 | 2,4-Dichlorophenyl | 2-Trifluoromethylphenyl | |
| 803 | 2,4-Dichlorophenyl | 3-Trifluoromethylphenyl | |
| 804 | 2,4-Dichlorophenyl | 4-Trifluoromethylphenyl | |
| 805 | 2,4-Dichlorophenyl | 4-Difluoromethoxyphenyl | |
| 806 | 2,4-Dichlorophenyl | 4-Trifluoromethoxyphenyl | |
| 807 | 2,4-Dichlorophenyl | 4-Tetrafluoroethoxyphenyl | |
| 808 | 2,4-Dichlorophenyl | 2-Fluorophenyl | |
| 809 | 2,4-Dichlorophenyl | 3-Fluorophenyl | |
| 810 | 2,4-Dichlorophenyl | 4-Fluorophenyl | |
| 811 | 2,4-Dichlorophenyl | 2,4-Difluorophenyl | |
| 812 | 2,4-Dichlorophenyl | 2-Chlorophenyl | |
| 813 | 2,4-Dichlorophenyl | 3-Chlorophenyl | |
| 814 | 2,4-Dichlorophenyl | 4-Chlorophenyl | |
| 815 | 2,4-Dichlorophenyl | 2,4-Dichlorophenyl | |
| 816 | 2,4-Dichlorophenyl | 3,4-Dichlorophenyl | |
| 817 | 2,4-Dichlorophenyl | 3,5-Dichlorophenyl | |
| 818 | 2,4-Dichlorophenyl | 2,4,6-Trichlorophenyl | |
| 819 | 2,4-Dichlorophenyl | 2-Chloro-4-fluorophenyl | |
| 820 | 2,4-Dichlorophenyl | 4-Chloro-2-fluorophenyl | |

TABLE-continued

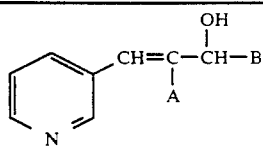

| Example No. | A | B | Phys. data (Fp. IR. ¹H-NMR) |
|---|---|---|---|
| 821 | 2,4-Dichlorophenyl | 4-Bromophenyl | |
| 822 | 2,4-Dichlorophenyl | Benzyl | |
| 823 | 2,4-Dichlorophenyl | 2-Methylbenzyl | |
| 824 | 2,4-Dichlorophenyl | 4-Methylbenzyl | |
| 825 | 2,4-Dichlorophenyl | 2,4-Dimethylbenzyl | |
| 826 | 2,4-Dichlorophenyl | 2-Fluorobenzyl | |
| 827 | 2,4-Dichlorophenyl | 3-Fluorobenzyl | |
| 828 | 2,4-Dichlorophenyl | 4-Fluorobenzyl | |
| 829 | 2,4-Dichlorophenyl | 2-Chlorobenzyl | |
| 830 | 2,4-Dichlorophenyl | 3-Chlorobenzyl | |
| 831 | 2,4-Dichlorophenyl | 4-Chlorobenzyl | |
| 832 | 2,4-Dichlorophenyl | 2,4-Dichlorobenzyl | |
| 833 | 2,4-Dichlorophenyl | 2-Chloro-4-fluorobenzyl | |
| 834 | 2,4-Dichlorophenyl | 2-Pyridyl | |
| 835 | 2,4-Dichlorophenyl | 3-Pyridyl | |
| 836 | 2,4-Dichlorophenyl | 4-Pyridyl | |
| 837 | 2,4-Dichlorophenyl | 5-Methyl-2-pyridyl | |
| 838 | 2,4-Dichlorophenyl | 6-Methyl-2-pyridyl | |
| 839 | 2,4-Dichlorophenyl | 6-Chloro-3-pyridyl | |
| 840 | 2,4-Dichlorophenyl | 5-Pyrimidinyl | |
| 841 | 2,4-Dichlorophenyl | 2-Pyrazinyl | |
| 842 | 2,4-Dichlorophenyl | 2-Thienyl | |
| 843 | 2,4-Dichlorophenyl | 3-Thienyl | |
| 844 | 2,4-Dichlorophenyl | 2-Furyl | |
| 845 | 2,4-Dichlorophenyl | 3-Furyl | |
| 846 | 4-Methoxyphenyl | Phenyl | |
| 847 | 4-Methoxyphenyl | 2-Methylphenyl | |
| 848 | 4-Methoxyphenyl | 3-Methylphenyl | |
| 849 | 4-Methoxyphenyl | 4-Methylphenyl | |
| 850 | 4-Methoxyphenyl | 2,4-Dimethylphenyl | |
| 851 | 4-Methoxyphenyl | 2,6-Dimethylphenyl | |
| 852 | 4-Methoxyphenyl | 2,4,6-Trimethylphenyl | |
| 853 | 4-Methoxyphenyl | 4-Ethylphenyl | |
| 854 | 4-Methoxyphenyl | 4-Isopropylphenyl | |
| 855 | 4-Methoxyphenyl | 4-tert-Butylphenyl | |
| 856 | 4-Methoxyphenyl | 1-Naphthyl | |
| 857 | 4-Methoxyphenyl | 2-Naphthyl | |
| 858 | 4-Methoxyphenyl | 4-Biphenyl | |
| 859 | 4-Methoxyphenyl | 4-(2'-Chlorobiphenyl) | |
| 860 | 4-Methoxyphenyl | 4-(4'-Chlorobiphenyl) | |
| 861 | 4-Methoxyphenyl | 2-Methoxyphenyl | |
| 862 | 4-Methoxyphenyl | 3-Methoxyphenyl | |
| 863 | 4-Methoxyphenyl | 4-Methoxyphenyl | |
| 864 | 4-Methoxyphenyl | 3,4-Dimethoxyphenyl | |
| 865 | 4-Methoxyphenyl | 3,4,5-Trimethoxyphenyl | |
| 866 | 4-Methoxyphenyl | 4-tert-Butoxyphenyl | |
| 867 | 4-Methoxyphenyl | 2-Trifluoromethylphenyl | |
| 868 | 4-Methoxyphenyl | 3-Trifluoromethylphenyl | |
| 869 | 4-Methoxyphenyl | 4-Trifluoromethylphenyl | |
| 870 | 4-Methoxyphenyl | 4-Difluoromethoxyphenyl | |
| 871 | 4-Methoxyphenyl | 4-Trifluoromethoxyphenyl | |
| 872 | 4-Methoxyphenyl | 4-Tetrafluoroethoxyphenyl | |
| 873 | 4-Methoxyphenyl | 2-Fluorophenyl | |
| 874 | 4-Methoxyphenyl | 3-Fluorophenyl | |
| 875 | 4-Methoxyphenyl | 4-Fluorophenyl | |
| 876 | 4-Methoxyphenyl | 2,4-Difluorophenyl | |
| 877 | 4-Methoxyphenyl | 2-Chlorophenyl | |
| 878 | 4-Methoxyphenyl | 3-Chlorophenyl | |
| 879 | 4-Methoxyphenyl | 4-Chlorophenyl | |
| 880 | 4-Methoxyphenyl | 2,4-Dichlorophenyl | |
| 881 | 4-Methoxyphenyl | 3,4-Dichlorophenyl | |
| 882 | 4-Methoxyphenyl | 3,5-Dichlorophenyl | |
| 883 | 4-Methoxyphenyl | 2,4,6-Trichlorophenyl | |
| 884 | 4-Methoxyphenyl | 2-Chloro-4-fluorophenyl | |
| 885 | 4-Methoxyphenyl | 4-Chloro-2-fluorophenyl | |
| 886 | 4-Methoxyphenyl | 4-Bromophenyl | |
| 887 | 4-Methoxyphenyl | Benzyl | |
| 888 | 4-Methoxyphenyl | 2-Methylbenzyl | |
| 889 | 4-Methoxyphenyl | 4-Methylbenzyl | |
| 890 | 4-Methoxyphenyl | 2,4-Dimethylbenzyl | |
| 891 | 4-Methoxyphenyl | 2-Fluorobenzyl | |
| 892 | 4-Methoxyphenyl | 3-Fluorobenzyl | |

TABLE-continued

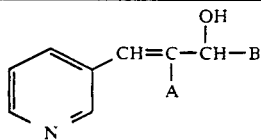

| Example No. | A | B | Phys. data (Fp. IR. $^1$H-NMR) |
|---|---|---|---|
| 893 | 4-Methoxyphenyl | 4-Fluorobenzyl | |
| 894 | 4-Methoxyphenyl | 2-Chlorobenzyl | |
| 895 | 4-Methoxyphenyl | 3-Chlorobenzyl | |
| 896 | 4-Methoxyphenyl | 4-Chlorobenzyl | |
| 897 | 4-Methoxyphenyl | 2,4-Dichlorobenzyl | |
| 898 | 4-Methoxyphenyl | 2-Chloro-4-fluorobenzyl | |
| 899 | 4-Methoxyphenyl | 2-Pyridyl | |
| 900 | 4-Methoxyphenyl | 3-Pyridyl | |
| 901 | 4-Methoxyphenyl | 4-Pyridyl | |
| 902 | 4-Methoxyphenyl | 5-Methyl-2-pyridyl | |
| 903 | 4-Methoxyphenyl | 6-Methyl-2-pyridyl | |
| 904 | 4-Methoxyphenyl | 6-Chloro-3-pyridyl | |
| 905 | 4-Methoxyphenyl | 5-Pyrimidinyl | |
| 906 | 4-Methoxyphenyl | 2-Pyrazinyl | |
| 907 | 4-Methoxyphenyl | 2-Thienyl | |
| 908 | 4-Methoxyphenyl | 3-Thienyl | |
| 909 | 4-Methoxyphenyl | 2-Furyl | |
| 910 | 4-Methoxyphenyl | 3-Furyl | |

The abovementioned compounds Ia where Ar is 3-pyridyl are also in principle obtainable for those where Ar is 5-pyrimidinyl, 2-pyrazinyl or 3-pyridazinyl as in the abovementioned synthesis examples.

The novel hetarylalkenes I have excellent activity against a broad spectrum of phytopathogenic fungi, in particular from the class consisting of the Ascomycetes and Basidiomycetes. Some of them have systemic activity and can be used as foliage or soil fungicides. They are of particular interest for controlling a large number of fungi on various crops or their seeds, in particular wheat, rye, barley, oats, rice, corn, lawns, cotton, soybean, coffee, sugar cane, fruit and ornamentals in horticulture, in viticulture and on vegetables, such as cucumbers, beans and cucurbitaceae.

The novel hetarylalkenes are particularly suitable for controlling the following harmful fungi:

Erysiphe graminis (powdery mildew) in cereals, Erysiphe cichoracearum and Sphaerotheca fuliginea in cucurbitaceae,
Podosphaera leucotricha in apples,
Uncinula necator on grapevines,
Puccinia species on cereals,
Rhizoctonia species on cotton and lawns,
Ustilago species on cereals and sugar cane,
Venturia inaequalis (scab) on apples,
Helminthosporium species on cereals,
Septoria nodorum on wheat,
Botrytis cinerea (gray mold) on strawberries and grapevines,
Cercospora arachidicola on peanuts,
Pseudocercosporella herpotrichoides on wheat and barley,
Pyricularia oryzae on rice,
Phytophthora infestans on potatoes and tomatoes,
Fusarium and Verticillium species on various plants,
Plasmopara viticola on grapevines and
Alternaria species on vegetables and fruit.

The hetarylalkenes are used by spraying or dusting the plants, materials or areas with the active ingredients or treating the seeds of the plants with the active ingredients. Application is effected before or after infection with the fungi.

The hetarylalkenes can be converted into the conventional fungicides (formulations), i.e. into solutions, emulsions, suspensions, dusts, powders, pastes and granules. The application forms depend entirely on the intended uses; they should in any case ensure a fine and uniform distribution of the active substance. The formulations are prepared in a known manner and using the conventional assistants, for example by extending the active ingredient with solvents and/or carriers, if necessary with the use of emulsifiers and dispersants. Suitable assistants for this purpose are essentially solvents, such as aromatics (e.g. xylene), chlorinated aromatics (e.g. chlorobenzenes), paraffins (e.g. mineral oil fractions), alcohols (e.g. methanol or butanol), ketones (e.g. cyclohexanone), amines (e.g. ethanolamine or dimethylformamide) and water (the latter if necessary together with organic solvents); carriers, such as ground natural minerals (e.g. kaolins, clays, talc or chalk) and ground synthetic minerals (eg. finely divided silica or silicates; emulsifiers, such as ionic and anionic emulsifiers (e.g. polyoxyethylene fatty alcohol ethers, alkylsulfonates and arylsulfonates) and dispersants, such as ligninsulfite waste liquors and methylcellulose.

The fungicides generally contain from 0.1 to 95, preferably from 0.5 to 90, % by weight of active ingredient. The application rates are from 0.02 to 3 kg of active ingredient per ha, depending on the type of effect desired.

The agents, if necessary after further dilution, are applied in a known manner, for example by spraying, atomizing, dusting, broadcasting, dressing or pouring.

Examples of formulations are:

I. 90 parts by weight of compound No. 66 are mixed with 10 parts by weight of N-methyl-α-pyrrolidone, and a solution which is suitable for use in the form of very small drops is obtained.

II. 20 parts by weight of compound No. 71 are dissolved in a mixture which consists of 80 parts by weight of xylene, 10 parts by weight of the adduct of from 8 to 10 moles of ethylene oxide with 1 mole of oleic acid N-monoethanolamide, 5 parts by weight of the calcium salt of dodecylbenzenesulfonic acid and 5 parts by weight of the adduct of 40 moles of ethylene oxide with 1 mole of castor oil. By pouring the solution into water and finely distributing it therein, an aqueous dispersion is obtained.

III. 20 parts by weight of compound No. 72 are dissolved in a mixture which consists of 40 parts by weight of cyclohexanone, 30 parts by weight of isobutanol and 20 parts by weight of the adduct of 40 moles of ethylene oxide with 1 mole of castor oil. By pouring the solution into water and finely distributing it therein, an aqueous dispersion is obtained.

IV. 20 parts by weight of compound No. 99 are dissolved in a mixture which consists of 25 parts by weight of cyclohexanol, 65 parts by weight of a mineral oil fraction boiling within a range from 210° to 280° C. and 10 parts by weight of the adduct of 40 moles of ethylene oxide with 1 mole of castor oil. By pouring the solution into water and finely distributing it therein, an aqueous dispersion is obtained.

V. 80 parts by weight of compound No. 131 are thoroughly mixed with 3 parts by weight of the sodium salt of diisobutylnaphthalene-α-sulfonic acid, 10 parts by weight of the sodium salt of a ligninsulfonic acid from a sulfite waste liquor and 7 parts by weight of silica gel powder, and the mixture is milled in a hammer mill. By finely distributing the mixture in water, a spray liquor is obtained.

VI. 3 parts by weight of compound No. 132 are thoroughly mixed with 97 parts by weight of finely divided kaolin. A dusting agent which contains 3% by weight of the active ingredient is obtained in this manner.

VII. 30 parts by weight of compound No. 134 are thoroughly mixed with a mixture consisting of 92 parts by weight of silica gel powder and 8 parts by weight of liquid paraffin, which has been sprayed onto the surface of this silica gel. A formulation of the active ingredient having good adhesion is obtained in this manner.

VIII. 40 parts by weight of compound No. 135 are thoroughly mixed with 10 parts by weight of the sodium salt of a phenolsulfonic acid/urea/formaldehyde condensate, 2 parts by weight of silica gel and 48 parts by weight of water. A stable aqueous dispersion is obtained. An aqueous dispersion is obtained by dilution with water.

IX. 20 parts by weight of compound No. 136 are thoroughly mixed with 2 parts by weight of the calcium salt of dodecylbenzenesulfonic acid, 8 parts by weight of a fatty alcohol polyglycol ether, 2 parts by weight of the sodium salt of a phenolsulfonic acid/urea/formaldehyde condensate and 68 parts by weight of a paraffinic mineral oil. A stable oily dispersion is obtained.

In these application forms, the novel agents may also be present together with other active ingredients, for example herbicides, insecticides, growth regulators and fungicides, or may be mixed with fertilizers and applied together with them. Mixing with fungicides results, in many cases, in an extension of the fungicidal action spectrum.

The following list of fungicides with which the novel compounds may be combined is intended to illustrate the possible combinations but not to impose any restrictions.

Sulfur,
dithiocarbamates and their derivatives, such as
 ferric dimethyldithiocarbamate,
 zinc dimethyldithiocarbamate,
 zinc ethylenebisdithiocarbamate,
 manganese ethylenebisdithiocarbamate,
 manganese zinc ethylenediamine bisdithiocarbamate,
 tetramethylthiuram disulfides,
 ammonia complex of zinc N,N-ethylenebisdithiocarbamate,
 ammonia complex of zinc N,N'-propylenebisdithiocarbamate,
 zinc N,N'-propylenebisdithiocarbamate and
 N,N'-propylenebis-(thiocarbamoyl) disulfide;
nitro derivatives, such as
 dinitro-(1-methylheptyl)-phenyl crotonate,
 2-sec-butyl-4,6-dinitrophenyl 3,3-dimethylacrylate,
 2-sec-butyl-4,6-dinitrophenyl isopropyl carbonate and diisopropyl 5-nitroisophthalate;
heterocyclic substances, such as
 2-heptadecyl-2-imidazoline acetate,
 2,4-dichloro-6-(o-chloroanilino)-s-triazine,
 O,O-diethyl phthalimidophosphonothioate,
 5-amino-1-[bis-(dimethylamino)-phosphinyl]-3-phenyl-1,2,4-triazole,
 2,3-dicyano-1,4-dithioanthraquinone,
 2-thio-1,3-dithio-(4,5-b)-quinoxaline,
 methyl 1-(butylcarbamoyl)-2-benzimidazolecarbamate,
 2-methoxycarbonylaminobenzimidazole,
 2-fur-2-ylbenzimidazole,
 2-thiazol-4-ylbenzimidazole,
 N-(1,1,2,2-tetrachloroethylthio)-tetrahydrophthalimide,
 N-trichloromethylthio tetrahydrophthalimide,
 N-trichloromethylthiophthalimide,
 N-dichlorofluoromethylthio-N°,N°-dimethyl-N-phenyl-sulfuric acid diamide,
 5-ethoxy-3-trichloromethyl-1,2,3-thiadiazole,
 2-thiocyanatomethylbenzothiazole,
 1,4-dichloro-2,5-dimethoxybenzene,
 -(2-chlorophenylhydrazono)-3-methyl-5-isoxazolone,
 pyridine-2-thio-1-oxide,
 8-hydroxyquinoline and its copper salt,
 2,3-dihydro-5-carboxanilido-6-methyl-1,4-oxathiine,
 2,3-dihydro-5-carboxanilido-6-methyl-1,4-oxathiine-4,4dioxide,
 2-methyl-5,6-dihydro-4H-pyran-3-carboxanilide,
 2-methylfuran-3-carboxanilide,
 2,5-dimethylfuran-3-carboxanilide,
 2,4,5-trimethylfuran-3-carboxanilide,
 2,5-dimethylfuran-3-carboxylic acid cyclohexylamide,
 N-cyclohexyl-N-methoxy-2,5-dimethylfuran-3-carboxamide,
 2-methylbenzanilide,
 2-iodobenzanilide,
 N-formyl-N-morpholine-2,2,2-trichloroethyl acetal,
 piperazine-1,4-diylbis-(1-(2,2,2-trichloroethyl)-formamide),
 1-(3,4-dichloroanilino)-1-formylamino-2,2,2-trichloroethane,
 2,6-dimethyl-N-tridecylmorpholine and its salts,
 2,6-dimethyl-N-cyclododecylmorpholine and its salts,
 N-[3-(p-tert-butylphenyl)-2-methylpropyl]-cis-2,6-dimethylmorpholine,
 N-[3-(p-tert-butylphenyl)-2-methylpropyl]-piperidine,
 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2ylethyl]-1H-1,2,4-triazole,
N-(n-propyl)-N-(2,4,6-trichlorophenoxyethyl)-N'-imidazol-ylurea,
1-(4-chlorophenoxy)-3,3-dimethyl-1-(1H-1,2,4-triazol-1-yl)-2-butanone,
1-(4-chlorophenoxy)-3,3-dimethyl-1-(1H-1,2,4-triazol-1-yl)-2-butanol,
α-(2-chlorophenyl)-α-(4-chlorophenyl)-5-pyrimidinemethanol,
5-butyl-2-dimethylamino-4-hydroxy-6-methylpyrimidine,
bis-(p-chlorophenyl)-3-pyridinemethanol,
1,2-bis-(3-ethoxycarbonyl-2-thioureido)-benzene and
1,2-bis-(3-methoxycarbonyl-2-thioureido)-benzene,
and various other fungicides, such as
dodecylguanidine acetate,
3-[3-(3,5-dimethyl-2-oxycyclohexyl)-2-hydroxyethyl]-glutarimide,
hexachlorobenzene,
methyl DL-N-(2,6-dimethylphenyl)-N-2-furoylalaninate,
methyl DL-N-(2,6-dimethylphenyl)-N-(2'-methoxyacetyl)-alanine,
N-(2,6-dimethylphenyl)-N-chloroacetyl-D,L-2-aminobutyrolactone,
methyl DL-N-(2,6-dimethylphenyl)-N-(phenylacetyl)-alanine,
5-methyl-5-vinyl-3-(3,5-dichlorophenyl)-2,4-dioxo-1,3-oxazolidine,
3-(3,5-dichlorophenyl)-5-methyl-5-methoxymethyl-1,3-oxazolidine-2,4-dione,
3-(3,5-dichlorophenyl)-1-isopropylcarbamoylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2-4-triazole,
2,4-difluoro-α-(1H-1,2,4-triazolyl-1-methyl)-benzhydryl alcohol,
N-(3-chloro-2,6-dinitro-4-trifluoromethylphenyl)-5-trifluoromethyl-3-chloro-2-aminopyridine and
1-((bis-(4-fluorophenyl)-methylsilyl)-methyl)-1H-1,2,4-triazole.

EXAMPLES OF USE

The fungicidal action of the hetarylalkenes I was compared with that of 2-(2,4-dichlorophenyl)-3-(3-pyridyl)-acrylic acid (A), disclosed in EP-A2-104 690, and 1(4-chlorophenyl)-3-(3-pyridyl)-prop-2-en-1-one (B), disclosed under CAS-Reg. No. 40665-19-8, in greenhouse experiments.

EXAMPLE A

Activity against Pyrenophora teres

The experiments were carried out using the active ingredients 66, 71, 72, 99, 100, 134, 135, 136, 137, 143, 262, 265, 273, 360, 490 and 555.

Barley seedlings of the Igri variety, in the two-leaf stage, were sprayed to run-off with aqueous suspensions which contained 80% of active ingredient and 20% of emulsifier, the percentages being based on dry substance. After 24 hours, the plants were inoculated with a spore suspension of the fungus Pyrenophora teres and were placed for 48 hours in a conditioned chamber at high atmospheric humidity and at 18° C. Thereafter, the plants were cultivated for a further 5 days in a greenhouse at 20°-22° C. and 70% relative humidity. The extent of development of the symptoms was then determined.

The result shows that, when applied as a 0.05% strength spray formulation, all active ingredients investigated have a better fungicidal action (90%) than the known comparative active ingredient (A) (40%).

EXAMPLE B

Activity against powdery mildew of cucumbers

The experiments were carried out using the active ingredients 295, 360, 490 and 555.

Young cucumber plants of the Chinesische Schlange variety, in the two-leaf stage, were sprayed with an aqueous conidia suspension of cucumber powdery mildew (Erysiphe cichoracearum and Sphaerotheca fuliginea). On the next day, these plants were sprayed to run-off with an aqueous spray liquor which contained 80% of active ingredient and 20% of emulsifier, the percentages being based on dry substance, and were placed in a greenhouse at from 20° to 22° C. and from 70 to 70% humidity. 21 days after application of the active ingredient, the extent of fungal attack was determined.

The result shows that, when applied as a 0.025% strength aqueous active ingredient formulation, all active ingredients investigated have better fungicidal action (95%) than the known comparative active ingredient (B) (0%).

EXAMPLE C

Activity against Botrytis cinerea

The experiments were carried out using the active ingredients 72, 136, 265, 273, 490 and 555.

After 4 or 5 leaves were well developed, pimento seedlings of the Neusiedler Ideal Elite variety were sprayed to run-off with aqueous suspensions which contained 80% of active ingredient and 20% of emulsifier, the percentages being based on dry substance. After the spray coating had dried off, the plants were sprayed with a conidia suspension of the fungus Botrytis cinerea and were placed in a chamber at high humidity and at from 22° to 24° C. After 5 days, the disease had developed on the untreated control plants to such an extent that the resulting leaf necroses covered the predominant part of the leaves.

The result shows that, when applied as a 0.05% strength aqueous active ingredient formulation, all active ingredients investigated have a better fungicidal action (90%) than the known comparative active ingredient (A) (40%).

We claim:

1. A hetarylalkene of the formula I

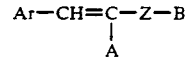

where
Ar is 3-pyridyl;
A is $C_1$-$C_6$-alkyl, $C_2$-$C_6$-alkenyl, $C_3$-$C_8$-cycloalkyl, $C_3$-$C_8$-cycloalkyl-$C_1$-$C_3$-alkyl or phenyl or phenyl or phenylalkyl, where phenyl in each case may be mono-substituted, disubstituted, or trisubstituted by $C_1$-$C_4$-alkyl, $C_1$-$C_4$-alkoxy, $C_1$-$C_4$-mono, di- or trihaloalkyl, $C_1$-$C_4$-haloalkoxy, phenyl or halogen:
Z is

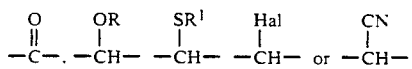

where
- R is hydrogen, $C_1$–$C_4$-alkyl, $C_2$–$C_4$-acyl, phenyl, benzyl or benzoyl, in which each of the phenyl rings may be monosubstituted, disubstituted or trisubstituted by $C_1$–$C_4$-alkyl, $C_1$–$C_4$-alkoxy, $C_1$–$C_4$-haloalkyl, $C_1$–$C_4$-haloalkoxy, halogen, cyano or nitro, or R is $C_1$–$C_4$-alkylsulfonyl or unsubstituted or $C_1$–$C_4$-alkyl-substituted phenylsulfonyl,
- $R^1$ is $C_1$–$C_4$-alkyl, phenyl or benzyl, where each of the phenyl rings may be mono-substituted, disubstituted or trisubstituted by $C_1$–$C_4$-alkyl, $C_1$–$C_4$-alkoxy, $C_1$–$C_4$-haloalkyl, $C_1$–$C_4$-haloalkoxy, halogen, cyano or nitro, and Hal is fluorine, chlorine, bromine or iodine; and
- B is aryl, or aralkyl wherein aryl in each case may be phenyl or naphthyl and in which each of the aromatic rings may be mono-substituted, disubstituted or trisubstituted by $C_1$–$C_4$-alkyl, $C_1$–$C_4$-haloalkyl, $C_1$–$C_4$-haloalkoxy, phenyl, halophenyl or halogen, and its N-oxides and addition salts with inorganic mineral acids, carboxylic acids or mononuclear aryl-sulfonic acids.

2. A hetarylalkenal of the formula III

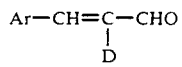 III where Ar is 3-pyridyl and D is $C_2$–$C_6$-alkyl, $C_3$–$C_8$-cycloalkyl, $C_3$–$C_8$-cycloalkyl-$C_1$–$C_3$-alkyl or mononuclear or dinuclear aryl $C_1$–$C_3$-alkyl, in which aryl may be mono-substituted, disubstituted, or trisubstituted by $C_1$–$C_4$-alkyl, $C_1$–$C_4$-alkoxy, $C_1$–$C_4$-haloalkyl, $C_1$–$C_4$-haloalkoxy, phenyl or halogen.

3. A fungicide containing a hetarylalkene, an N-oxide or an acid addition salt as claimed in claim 1 and conventional additives.

4. A method for controlling harmful fungi, wherein the fungi or the plants, seeds, materials, or areas threatened by fungal attack are treated with a fungicidally effective amount of a hetarylalkene of the formula I'

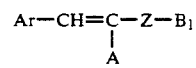 I' where
- Ar is 3-pyridyl;
- A is $C_1$–$C_6$-alkyl, $C_2$–$C_6$-alkenyl, $C_3$–$C_8$-cycloalkyl, $C_3$–$C_8$-cycloalkyl-$C_1$–$C_3$-alkyl or phenyl or phenylalkyl, where phenyl in each case may be mono-substituted, disubstituted, or trisubstituted by $C_1$–$C_4$-alkyl, $C_1$–$C_4$-alkoxy, $C_1$–$C_4$-mono-, di- or trihaloalkyl, $C_1$–$C_4$-haloalkoxy, phenyl or halogen;
- Z is

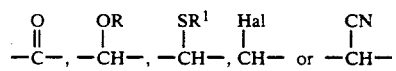

where
- R is hydrogen, $C_1$–$C_4$-alkyl, $C_2$–$C_4$-acyl, phenyl, benzyl or benzoyl, in which each of the phenyl rings may be monosubstituted, disubstituted or trisubstituted by $C_1$–$C_4$-alkyl, $C_1$–$C_4$-alkoxy, $C_1$–$C_4$-haloalkyl, $C_1$–$C_4$-haloalkoxy, halogen, cyano or nitro, or R is $C_1$–$C_4$-alkylsulfonyl or unsubstituted or $C_1$–$C_4$-alkyl-substituted phenylsulfonyl,
- $R^1$ is $C_1$–$C_4$-alkyl, phenyl or benzyl, where each of the phenyl rings may be mono-substituted, disubstituted or trisubstituted by $C_1$–$C_4$-alkyl, $C_1$–$C_4$-alkoxy, $C_1$–$C_4$-haloalkyl, $C_1$–$C_4$-haloalkoxy, halogen, cyano or nitro, and Hal is fluorine, chlorine, bromine or iodine; and
- $B_1$ is aryl, or aralkyl wherein aryl in each case may be phenyl or naphthyl and in which each of the aromatic rings may be mono-substituted, disubstituted or trisubstituted by $C_1$–$C_4$-alkyl, $C_1$–$C_4$-alkoxy, $C_1$–$C_4$-haloalkyl, $C_1$–$C_4$-haloalkoxy, phenyl, halophenyl or halogen, and its N-oxides and addition salts with inorganic mineral acids, carboxylic acids or mononuclear aryl-sulfonic acids; or with a fungicide containing a hetarylalkene of formula I' as defined above, an N-oxide or an acid addition salt and conventional additives.

* * * * *